(12) United States Patent
Upshaw et al.

(10) Patent No.: US 9,469,607 B2
(45) Date of Patent: Oct. 18, 2016

(54) POLYTHIOLS WITH CARBAMATE GROUPS

(71) Applicant: Chevron Phillips Chemical Company LP, The Woodlands, TX (US)

(72) Inventors: Thomas A. Upshaw, Tulsa, OK (US); Michael S. Matson, Bartlesville, OK (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 100 days.

(21) Appl. No.: 14/636,747

(22) Filed: Mar. 3, 2015

(65) Prior Publication Data

US 2016/0257647 A1    Sep. 8, 2016

(51) Int. Cl.
| | |
|---|---|
| *C07C 319/02* | (2006.01) |
| *C07C 323/12* | (2006.01) |
| *C07C 269/02* | (2006.01) |
| *C07C 271/24* | (2006.01) |
| *C07C 271/10* | (2006.01) |
| *C08G 18/28* | (2006.01) |

(52) U.S. Cl.
CPC ........... *C07C 323/12* (2013.01); *C07C 269/02* (2013.01); *C07C 319/02* (2013.01); *C07C 271/10* (2013.01); *C07C 271/24* (2013.01); *C08G 18/2835* (2013.01)

(58) Field of Classification Search
None
See application file for complete search history.

(56) References Cited

U.S. PATENT DOCUMENTS

| | | | |
|---|---|---|---|
| 3,883,598 A | 5/1975 | Guthrie et al. | |
| 3,966,794 A | 6/1976 | Larsen | |
| 3,976,553 A | 8/1976 | Larsen | |
| 3,981,901 A | 9/1976 | Guthrie et al. | |
| 3,984,456 A | 10/1976 | Guthrie et al. | |
| 3,996,257 A | 12/1976 | Larsen | |
| 4,045,317 A | 8/1977 | Larsen | |
| 4,045,472 A | 8/1977 | Guthrie et al. | |
| 4,117,017 A * | 9/1978 | Morgan | C07C 43/178 522/97 |
| 7,910,666 B2 | 3/2011 | Byers et al. | |
| 7,989,655 B2 | 8/2011 | Refvik et al. | |
| 8,003,748 B2 | 8/2011 | Byers et al. | |
| 8,389,608 B2 | 3/2013 | Upshaw et al. | |
| 8,461,293 B2 | 6/2013 | Matson et al. | |
| 2008/0194720 A1 | 8/2008 | Stappers et al. | |
| 2014/0131618 A1 | 5/2014 | Matson | |

FOREIGN PATENT DOCUMENTS

| | | |
|---|---|---|
| GB | 1 510 594 | 5/1978 |
| GB | 1 510 595 | 5/1978 |
| JP | 54-003843 | 1/1979 |
| WO | WO 2011/163317 | 12/2011 |

OTHER PUBLICATIONS

International Search Report and the Written Opinion of the International Searching Authority in PCT/US2016/020237 dated May 18, 2016, 9 pages.
Tempelaar, et al., "Synthesis of Allyl-Functional Poly(carbonates) and their Post-Polymerization Functionalization by Radical 'Thiol-ene' Chemistry," Polymeric Materials: Science & Engineering (2011), pp. 104, 459.
Senyurt et al., "Thermal and Mechanical Properties of Cross-Linked Photopolymers Based on Multifunctional Thiol-Urethane Ene Monomers," Macromolecules (2007), vol. 40, No. 9, pp. 3174-3182.

\* cited by examiner

*Primary Examiner* — Tanisha Diggs
(74) *Attorney, Agent, or Firm* — Merchant & Gould PC

(57) ABSTRACT

The present invention discloses polythiol compositions containing sulfur-containing compounds with carbamate groups, and to methods for producing such polythiol compositions. These polythiol compositions can be synthesized via the reaction of an isocyanate with an allyl ether alcohol, followed by thiolation with $H_2S$, and these polythiol compositions are often used in formulations for adhesives, paints, and coatings.

20 Claims, No Drawings

POLYTHIOLS WITH CARBAMATE GROUPS

BACKGROUND OF THE INVENTION

The present invention relates generally to polythiol compositions containing sulfur-containing compounds with carbamate groups, and to methods for producing such polythiol compositions. These polythiol compositions can be used as curing agents in adhesives, paints, coatings, and other end-use applications.

SUMMARY OF THE INVENTION

This summary is provided to introduce a selection of concepts in a simplified form that are further described in the detailed description. This summary is not intended to identify required or essential features of the claimed subject matter. Nor is this summary intended to be used to limit the scope of the claimed subject matter.

Various polythiol compositions comprising sulfur-containing compounds are disclosed herein. In one embodiment, a polythiol composition comprising sulfur-containing compounds is disclosed, and in this embodiment, the sulfur-containing compounds can have formula (I):

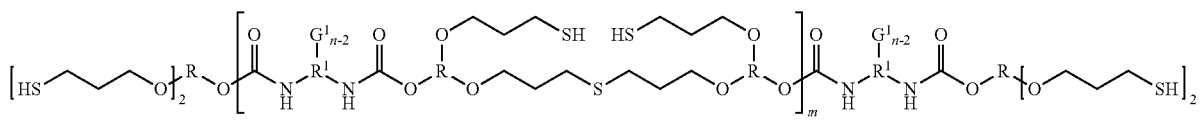

In formula (I), $G^1$ can have formula (II):

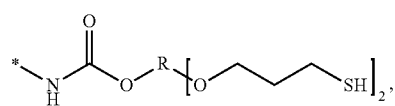

each R independently can be any $C_3$ to $C_{15}$ hydrocarbon group disclosed herein, each $R^1$ independently can be any $C_1$ to $C_{30}$ hydrocarbon group disclosed herein, n can be any integer greater than or equal to 2 disclosed herein, and m can be any integer from 0 to 6 disclosed herein, wherein an average value of m in the composition can range from greater than 0 to 3.

Processes for forming polythiol compositions also are disclosed herein. Generally, these processes can comprise (1) contacting a compound having formula (A):

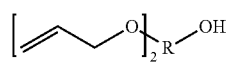

with a compound having formula (B):

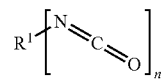

to form a reaction mixture comprising a polycarbamate; and (2) contacting the polycarbamate, $H_2S$, and an optional phosphite compound to form the polythiol composition. The molar ratio of $H_2S$ to carbon-carbon double bonds of the polycarbamate can be in any range from 2:1 to 500:1 disclosed herein. The polythiol composition can comprise sulfur-containing compounds having formula (I):

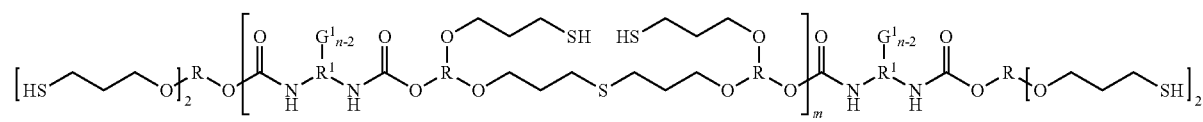

In formula (I), $G^1$ can have formula (II):

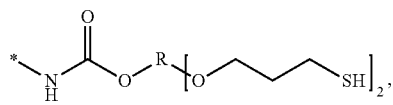

each R independently can be any $C_3$ to $C_{15}$ hydrocarbon group disclosed herein, each $R^1$ independently can be any $C_1$ to $C_{30}$ hydrocarbon group disclosed herein, n can be any integer greater than or equal to 2 disclosed herein, and m can be any integer from 0 to 6 disclosed herein, wherein an average value of m in the composition can range from greater than 0 to 3.

Both the foregoing summary and the following detailed description provide examples and are explanatory only. Accordingly, the foregoing summary and the following detailed description should not be considered to be restrictive. Further, features or variations can be provided in addition to those set forth herein. For example, certain embodiments can be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2$^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, a feedstock consisting essentially of material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a reaction mixture consisting of specific components; alternatively, consisting essentially of specific components; or alternatively, comprising the specific components and other non-recited components. While compositions and methods are described herein in terms of "comprising" various components or steps, the compositions and methods can also "consist essentially of" or "consist of" the various components or steps, unless stated otherwise. For example, a polythiol composition consistent with embodiments of the present invention can comprise; alternatively, can consist essentially of; or alternatively, can consist of; sulfur-containing compounds having formula (I).

The terms "a," "an," and "the" are intended to include plural alternatives, e.g., at least one. For instance, the disclosure of "a solvent," "a phosphite compound," etc., is meant to encompass one, or mixtures or combinations of more than one, solvent, phosphite compound, etc., unless otherwise specified.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; pentane includes n-pentane, 2-methyl-butane, and 2,2-dimethylpropane; a general reference to a butyl group includes an n-butyl group, a sec-butyl group, an iso-butyl group, and a t-butyl group; and a general reference to 2,3-pentanediol includes 2R,3R-pentanediol, 2S,3S-pentanediol, 2R,3S-pentanediol, and mixtures thereof.

In one embodiment, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogen atoms, as necessary for the situation, removed from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbyl group" is used herein in accordance with the definition specified by IUPAC: a univalent group formed by removing a hydrogen atom from a hydrocarbon (i.e., containing only carbon and hydrogen). A "hydrocarbyl group" can be acyclic or cyclic, and/or linear or branched. A "hydrocarbyl group" can include rings, ring systems, aromatic rings, and aromatic ring systems, which contain only carbon and hydrogen. "Hydrocarbyl groups" include, by way of example, aryl, alkyl, cycloalkyl, and alkylaryl/arylalkyl groups, amongst other groups as members. As used herein, a "hydrocarbon group" refers to a generalized group formed by removing one or more hydrogen atoms (as necessary for the particular group to conform to the rules of chemical value) from a hydrocarbon. A "hydrocarbon group" encompasses, by way of example, arene groups, alkane groups, cycloalkane groups, aralkane groups, amongst other groups as members. A "cyclohydrocarbon" encompasses, by way of example, aromatic hydrocarbon rings and ring systems, and cyclic aliphatic hydrocarbons, amongst other groups as members.

An aliphatic compound is an acyclic or cyclic, saturated or unsaturated compound, excluding aromatic compounds. That is, an aliphatic compound is a non-aromatic organic compound. Aliphatic compounds, and therefore aliphatic groups, can contain organic functional group(s) and/or atom(s) other than carbon and hydrogen. An "aliphatic group" is a generalized group formed by removing one or more hydrogen atoms (as necessary for the particular group) from a carbon atom of an aliphatic compound.

An "aromatic group" refers to a generalized group formed by removing one or more hydrogen atoms (as necessary for the particular group to conform to the rules of chemical valence, and at least one of which is an aromatic ring carbon atom) from an aromatic compound. Aromatic compounds and aromatic groups can be monocyclic or polycyclic, unless otherwise specified. Aromatic compounds include "arenes" (hydrocarbon aromatic compounds) and "heteroarenes" (heteroaromatic compounds). Examples of arenes include, but are not limited to, benzene, naphthalene, and toluene, among others. Examples of heteroarenes include, but are not limited to furan, pyridine, and methylpyridine, among others.

The term "alkyl group" is used herein in accordance with the definition specified by IUPAC: a univalent group formed by removing a hydrogen atom from an alkane. An "alkane group" is a general term that refers to a group formed by removing one or more hydrogen atoms (as necessary for the particular group to conform to conform to the rules of chemical valence) from an alkane. An "alkyl group" and an "alkane group" can be an acyclic or cyclic group, and/or may be linear or branched, unless otherwise specified.

A cycloalkane is a saturated cyclic hydrocarbon, with or without side chains, for example, cyclobutane and methylcyclobutane. Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. A "cycloalkyl group" is a univalent group derived by removing a hydrogen atom from a ring carbon atom from a cycloalkane. A "cycloalkane group" refers to a generalized group formed by removing one or more hydrogen atoms (as necessary for the particular group to conform to the rules of chemical valence, and at least one of which is a ring carbon) from a cycloalkane.

As used herein, "thiol sulfur" means sulfur from a —SH group (thiol group), while "sulfide sulfur" means sulfur from a —S— group (sulfide group). Sulfide sulfur groups encompass both intermolecular sulfide groups and intramolecular sulfide groups. The term "intermolecular sulfide" as used herein refers to sulfide bonds formed by a reaction between two molecules. The term "intramolecular sulfide" refers to sulfide bonds formed by a reaction within a single molecule.

As used herein, a "polythiol composition" refers to a composition comprising polythiol molecules. Polythiol molecules refer to molecules having two or more thiol groups per molecule (e.g., 2, 3, 4, 5, etc., thiol groups). For illustrative purposes, in addition to polythiol molecules having 2 or more SH groups, a polythiol composition also can contain compounds having only 1 thiol group, compounds having only one sulfur atom present as sulfide sulfur, etc. Furthermore, such polythiol compositions can contain other compounds and components, non-limiting examples of which can include solvents and other materials, as well as residual polycarbamate from which the polythiol composition can be derived.

In some instances, the polythiol composition can be described, while in others, the sulfur-containing compounds (i.e., having at least 1 sulfur atom present as thiol sulfur or sulfide sulfur) of the polythiol composition can be described. Consequently, within this disclosure, properties associated with polythiol compositions can include contributions from the polycarbamate from which the compositions can be formed, as well as other reactants and by-products. In some circumstances, it can be beneficial to refer only to the sulfur-containing compounds, as if the polycarbamate, other reactants, by-products, and/or solvent are not present in the composition. Accordingly, within this disclosure, the term "sulfur-containing compounds," used in conjunction with the polythiol composition, refers to organic compounds within the composition that contain at least one sulfur atom present in a thiol sulfur group or sulfide sulfur group, and excludes any non-sulfur-containing compound (e.g., polycarbamate reactant and/or solvent, among others), and excludes any sulfur-containing reactant (e.g., $H_2S$). In sum, a polythiol composition can include all materials in a composition comprising polythiol molecules, while the sulfur-containing compounds refer only to the compounds within the polythiol composition having at least sulfur atom present as a —SH or a —S— group.

As utilized herein, the thiol or mercaptan equivalent weight (SHEW) equals the molecular weight of a particular mercaptan molecule divided by the number of mercaptan groups in the mercaptan molecule, and has the units of grams/equivalent (g/eq). When referring to a composition of sulfur-containing compounds, the SHEW refers to an average SHEW of all the sulfur-containing compounds in the composition.

Olefinic double bonds (i.e., —C=C—) are non-aromatic double bonds, but the olefinic double bonds may be either conjugated or non-conjugated, and may be located at any position (e.g., terminally or internally) in the hydrocarbon compound or hydrocarbon group, unless specified otherwise or the context requires otherwise.

The terms "contact product," "contacting," and the like, are used herein to describe compositions and methods wherein the components are contacted together in any order, in any manner, and for any length of time. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION OF THE INVENTION

The present invention provides polythiol compositions containing sulfur-containing compounds with carbamate groups, and to methods for producing such polythiol compositions. While not wishing to be bound by theory, a potential benefit of these polythiol compositions comprising sulfur-containing compounds, as described herein, is higher reactivity and a faster cure time for epoxy resins, as compared to that of current amine curing technology. Additionally, improvements in weatherability and toughness are expected. A significant feature of particular polythiol compositions disclosed herein is the presence of sulfur-containing compounds having multiple carbamate groups, multiple thiol groups, and at least one —S— group (sulfide group), and potential benefits of these polythiol compositions can include, but are not limited to, increased mercaptan equivalent weight, and/or increased functionality, and/or higher average molecular weight, and/or increased viscosity, and/or lower vapor pressure, as compared to other polythiol compositions that do not comprise sulfur-containing compounds with a sulfide group (—S— group). Additionally, the processes disclosed herein to produce such compositions are believed to be superior to other processes due to fewer process steps, reduced waste, and less burdensome purification requirements.

Polythiol Compositions

Polythiol compositions consistent with embodiments of the invention disclosed and described herein can comprise sulfur-containing compounds, and these sulfur-containing compounds can comprise compounds having the structure of formula (I):

each R independently can be a $C_3$ to $C_{15}$ hydrocarbon group, each $R^1$ independently can be a $C_1$ to $C_{30}$ hydrocarbon group, n can be an integer greater than or equal to 2, and m can be an integer from 0 to 6. In an embodiment, the sulfur-containing compounds can have formula (I) and an average value of m in the composition can range from greater than 0 to 3.

Unless otherwise specified, formula (I) above, any other structural formulas disclosed herein, and any complex, compound, or species disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In formula (I), each $R^1$ independently can be any $C_1$-$C_{30}$ hydrocarbon group, or alternatively, any non-olefinic $C_1$-$C_{30}$ hydrocarbon group, that conforms to the rules of chemical valence. In one embodiment, each $R^1$ independently can be a $C_1$ to $C_{20}$ hydrocarbon group, a non-olefinic $C_1$ to $C_{20}$ hydrocarbon group, a $C_1$ to $C_{15}$ hydrocarbon group, a non-olefinic $C_1$ to $C_{15}$ hydrocarbon group, a $C_1$ to $C_{10}$ hydrocarbon group, or a non-olefinic $C_1$ to $C_{10}$ hydrocarbon group. In another embodiment, each $R^1$ independently can be a $C_1$ to $C_{30}$ alkane group, a $C_1$ to $C_{20}$ alkane group, a $C_1$ to $C_{15}$ alkane group, a $C_1$ to $C_{10}$ alkane group, or a $C_1$ to $C_6$ alkane group. For instance, the alkane group which can be $R^1$ in formula (I) independently can be a methane group, an ethane group, a propane group, a butane group, a pentane group, a hexane group, a heptane group, an octane group, a nonane group, a decane group, a undecane group, a dodecane group, a tridecane group, a tetradecane group, a pentadecane group, a hexadecane group, a heptadecane group, or an octadecane group; or alternatively, a methane group, an ethane group, a propane group, a butane group, a pentane group, a hexane group, a heptane group, an octane group, a nonane group, or a decane group. Consistent with embodiments of this invention, each $R^1$ independently can be linear or branched; alternatively, linear; or alternatively, branched.

In another embodiment, each $R^1$ independently can be an aliphatic $C_4$ to $C_{30}$ cyclohydrocarbon group, an aliphatic $C_5$

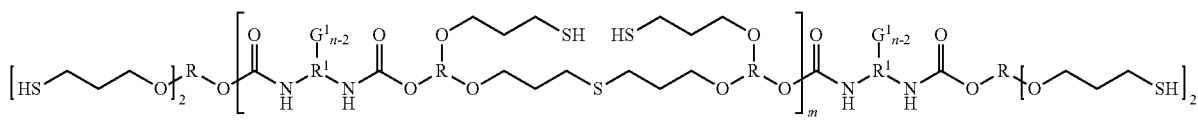

Within formula (I), $G^1$, each R, each $R^1$, n, and m are independent elements of the sulfur-containing compounds. Accordingly, the sulfur-containing compounds encompassed by formula (I) may be described using any combination of $G^1$, R, n, and m disclosed herein. In an embodiment, the sulfur-containing compound having formula (I) can have a structure where $G^1$ can have formula (II):

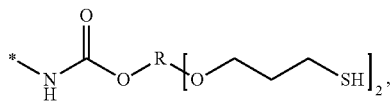

to $C_{20}$ cyclohydrocarbon group, or an aliphatic $C_6$ to $C_{12}$ cyclohydrocarbon group. In yet another embodiment, each $R^1$ independently can be a $C_4$ to $C_{30}$ cycloalkane group, a $C_5$ to $C_{20}$ cycloalkane group, or a $C_6$ to $C_{12}$ cycloalkane group. For instance, each $R^1$ independently can be a cyclobutane group, a substituted cyclobutane group, a cyclopentane group, a substituted cyclopentane group, a cyclohexane group, a substituted cyclohexane group, a cycloheptane group, a substituted cycloheptane group, a cyclooctane group, or a substituted cyclooctane group; alternatively, a cyclopentane group, a substituted cyclopentane group, a cyclohexane group, or a substituted cyclohexane group; alternatively, a cyclobutane group or a substituted cyclobutane group; alternatively, a cyclopentane group or a substituted cyclopentane group; alternatively, a cyclohexane group or a substituted cyclohexane group; alternatively, a cycloheptane group or a substituted cycloheptane group; alternatively, a cyclooctane group or a substituted cyclooctane group; alternatively, a cyclopentane group; alternatively, a substituted cyclopentane group; alternatively, a cyclohexane group; or alternatively, a substituted cyclohexane group. Substituents which can be utilized for the substituted cycloalkane group are independently disclosed herein and can be utilized without limitation to further describe the substituted cycloalkane group which can be $R^1$ in formula (I).

In another embodiment, each $R^1$ independently can be a $C_6$ to $C_{30}$ aromatic group, a $C_6$ to $C_{20}$ aromatic group, a $C_6$ to $C_{12}$ aromatic group, or a $C_6$ to $C_9$ aromatic group, and such aromatic groups can be substituted or unsubstituted. For instance, each $R^1$ independently can be a benzene group, a toluene group, a xylene group (including ortho-xylene, meta-xylene, para-xylene), an ethylbenzene group, a naphthalene group, as well as substituted analogs of any of these aromatic groups. Substituents which can be utilized for the substituted aromatic groups are independently disclosed herein and can be utilized without limitation to further describe the substituted aromatic groups which can be $R^1$ in formula (I).

In accordance with embodiments of this invention, each non-hydrogen substituent for the substituted cycloalkane group or substituted aromatic group which can be $R^1$ in formula (I) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkane groups or substituted aromatic groups which can be $R^1$ in formula (I). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group. Furthermore, the hydrocarbyl substituent can be a benzyl group, a phenyl group, a tolyl group, or a xylyl group. Other appropriate substituents are readily apparent from this disclosure.

As described herein, each $R^1$ in formula (I) can be the same or different. In particular embodiments of this invention, each $R^1$ can be the same. As one of skill in the art would readily recognize, each $R^1$ can be the same when a single isocyanate starting material (a single compound having formula (B)) is utilized in the process for producing a polythiol composition, as described further herein.

In formulas (I) and (II), each R independently can be any $C_3$-$C_{15}$ hydrocarbon group, or alternatively, any non-olefinic $C_3$-$C_{15}$ hydrocarbon group, that conforms to the rules of chemical valence. While not limited thereto, the $C_3$ to $C_{15}$ hydrocarbon group and $C_3$ to $C_{15}$ non-olefinic hydrocarbon group which can be a R in formulas (I) and (II) can be any hydrocarbon or non-olefinic hydrocarbon group disclosed herein having from three to fifteen carbon atoms (e.g., as pertaining to $R^1$ in formula (I)). In one embodiment, for instance, each R independently can be a $C_3$ to $C_{12}$ hydrocarbon group, a non-olefinic $C_3$ to $C_{12}$ hydrocarbon group, a $C_3$ to $C_{10}$ hydrocarbon group, a non-olefinic $C_3$ to $C_{10}$ hydrocarbon group, a $C_3$ to $C_8$ hydrocarbon group, or a non-olefinic $C_3$ to $C_8$ hydrocarbon group. In another embodiment, each R independently can be a $C_3$ to $C_{15}$ alkane group, a $C_3$ to $C_{12}$ alkane group, a $C_3$ to $C_{10}$ alkane group, a $C_3$ to $C_8$ alkane group, or a $C_3$ to $C_6$ alkane group. Examples of such alkane groups can include, but are not limited to, a propane group, a butane group, a pentane group, a hexane group, a heptane group, an octane group, a nonane group, a decane group, and so forth.

Consistent with embodiments of this invention, each R independently can be linear or branched; alternatively, linear; or alternatively, branched. Moreover, each R independently can be acyclic or cyclic; alternatively, acyclic; or alternatively, cyclic (e.g., substituted or unsubstituted cycloalkane groups such as a cyclopentane group, a substituted cyclopentane group, a cyclohexane group, a substituted cyclohexane group, and the like).

As described herein, each R in formulas (I) and (II) can be the same or different. In particular embodiments of this invention, each R can be the same. As one of skill in the art would readily recognize, each R can be the same when a single starting material having formula (A) is utilized in the process for producing a polythiol composition, as described further herein.

In formula (I), n can be an integer greater than or equal to 2. In one embodiment, n can be an integer from 2 to 4, while in another embodiment, n can be an integer from 2 to 3. Yet, in another embodiment, n can be equal to 2; alternatively, n can be equal to 3; or alternatively, n can be equal to 4. Generally, in the polythiol compositions of this invention, the average value of n in the composition can be in a range from 2 to 4, or in a range from 2 to 3, or in a range from 2 to 2.5. As one of skill in the art would readily recognize, when the integer n is equal to 2, the $G^1$ moiety having formula (II) is not present in the compound having formula (I). In such circumstances, the polythiol composition can comprise sulfur-containing compounds having formula (III):

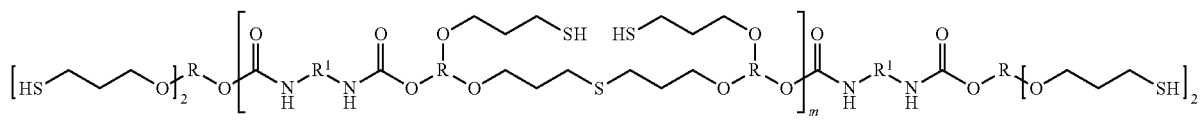

In formulas (I) and (III), m can be an integer in a range from 0 to 6. In various embodiments of this invention, m can be an integer from 0 to 4, an integer from 0 to 3, an integer from 0 to 2, or an integer from 0 to 1. Generally, in the polythiol compositions of this invention, the average value of m in the composition can fall within a range from greater than 0 up to and including 3. Alternatively, the average value of m in the compositions can be in a range from greater than 0 to less than 3, from greater than 0 to 2.5, from greater than 0 to 2, from greater than 0 to 1, or from greater than 0 to 0.5.

Polythiol compositions consistent with certain embodiments of this invention can contain a sulfur-containing compound having the following structure:

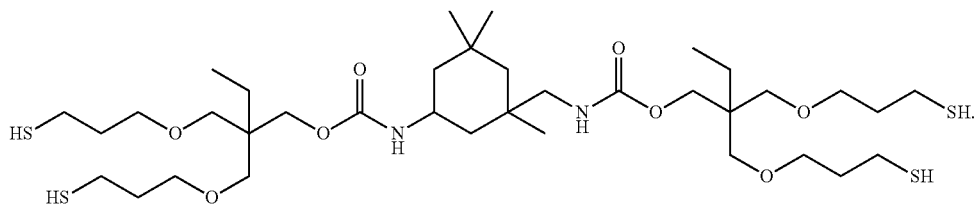 [SMILES: CCC(COCCCS)(COCCCS)COC(=O)NCC1(C)CC(NC(=O)OCC(CC)(COCCCS)COCCCS)CC(C)(C)C1]

Further, polythiol compositions consistent with certain embodiments of this invention can comprise sulfur-containing compounds having the following structures:

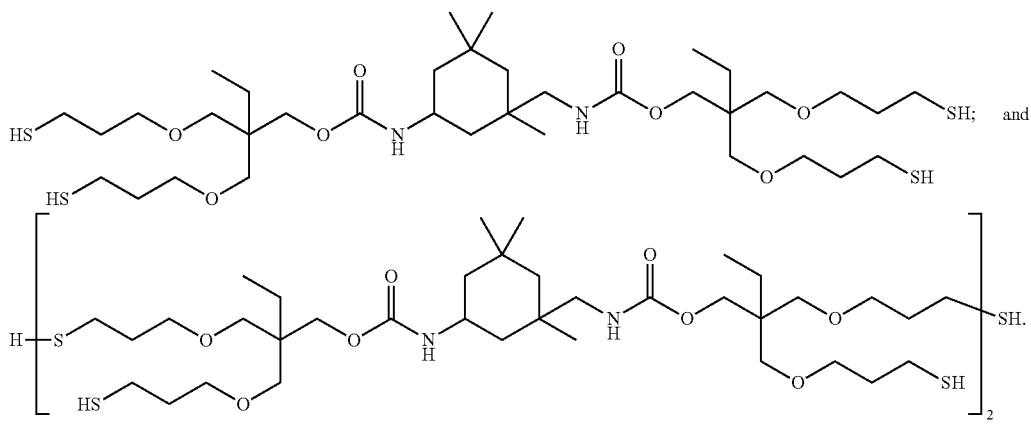

These illustrative and non-limiting examples of polythiol compositions comprising sulfur-containing compounds consistent with the present invention also can have any of the characteristics or properties provided herein, and in any combination.

In an embodiment, the sulfur-containing compounds of the polythiol composition can have a minimum average thiol sulfur (—SH) to sulfide sulfur (—S—) molar ratio of 2:1, 3:1, 4:1, 5:1, 10:1, 15:1, or 25:1; additionally or alternatively, the sulfur-containing compounds can have a maximum average thiol sulfur to sulfide sulfur molar ratio of 500:1, 250:1, 150:1, 100:1, 75:1, or 50:1. Generally, the sulfur-containing compounds of the polythiol composition can have an average thiol sulfur to sulfide sulfur molar ratio ranging from any minimum molar ratio disclosed herein to any maximum molar ratio disclosed herein. Therefore, suitable non-limiting ranges for the average thiol sulfur to sulfide sulfur molar ratio can include the following ranges: from 2:1 to 500:1, from 2:1 to 250:1, from 2:1 to 100:1, from 2:1 to 75:1, from 3:1 to 500:1, from 3:1 to 250:1, from 3:1 to 100:1, from 3:1 to 50:1, from 5:1 to 500:1, from 5:1 to 250:1, from 5:1 to 150:1, from 5:1 to 75:1, from 10:1 to 250:1, from 10:1 to 100:1, from 25:1 to 250:1, or from 25:1 to 50:1. Other appropriate ranges for the average thiol sulfur to sulfide sulfur molar ratio are readily apparent from this disclosure.

The polythiol compositions can be further characterized by the amount of sulfide sulfur (sulfur from a —S— group) present in the sulfur-containing compounds of the composition. For instance, sulfur-containing compounds of the composition can have an average of from 0.05 wt. % to 10 wt. % sulfide sulfur. These percentages are based on the total sulfur-containing compounds of the composition, regardless of the number of thiol and/or sulfide groups. In certain embodiments, the sulfur-containing compounds of the polythiol composition can have a minimum average sulfide sulfur content of 0.05, 0.1, 0.15, 0.2. 0.25, or 0.5 wt. %; additionally or alternatively, the sulfur-containing compounds can have a maximum average sulfide sulfur content of 10, 9, 8, 7, 6, 5, 4, 3, or 2 wt. %. Generally, the sulfur-containing compounds of the polythiol composition can have an average sulfide sulfur content in a range from any minimum average sulfide sulfur content to any maximum sulfide sulfur content disclosed herein. Therefore, suitable non-limiting ranges for the average sulfide sulfur content of the sulfur-containing compounds can include the following ranges: from 0.05 to 10 wt. %, from 0.05 to 7 wt. %, from 0.05 to 5 wt. %, from 0.05 to 2 wt. %, from 0.1 to 10 wt. %, from 0.1 to 8 wt. %, from 0.1 to 5 wt. %, from 0.1 to 3 wt. %, from 0.1 to 2 wt. %, from 0.25 to 10 wt. %, from 0.25 to 8 wt. %, from 0.25 to 6 wt. %, from 0.25 to 3 wt. %, from 0.5 to 10 wt. %, from 0.5 to 8 wt. %, from 0.5 to 6 wt. %, from 0.5 to 4 wt. %, from 0.5 to 3 wt. %, or from 0.5 to 2 wt. %. Other appropriate ranges for the average sulfide sulfur content are readily apparent from this disclosure.

Moreover, the polythiol compositions can be further characterized by the amount of thiol sulfur (sulfur from a —SH group) present in the sulfur-containing compounds of the composition. For example, sulfur-containing compounds of the composition can have an average of from 10 wt. % to 20 wt. % thiol sulfur. These percentages are based on the total sulfur-containing compounds, regardless of the number of thiol and/or sulfide groups. In particular embodiments, the sulfur-containing compounds of the polythiol composition can have a minimum average thiol sulfur content of 10, 11, 12, 12.5, 13, 13.5, or 14 wt. %; additionally or alternatively, the sulfur-containing compounds can have a maximum average thiol sulfur content of 20, 19, 18, 17, 16.5, 16.2, 16, 15.5, or 15 wt. %. Generally, the sulfur-containing compounds of the polythiol composition can have an average thiol sulfur content in a range from any minimum average thiol sulfur content to any maximum average thiol sulfur content disclosed herein. Therefore, suitable non-limiting ranges for the average thiol sulfur content of the sulfur-containing compounds can include the following ranges: from 10 to 20 wt. %, from 11 to 19 wt. %, from 12 to 18 wt. %, from 12 to 17 wt. %, from 12.5 to 16.5 wt. %, from 12.5 to 16.2 wt. %, from 12.5 to 16 wt. %, from 12.5 to 15.5 wt. %, from 12.5 to 15 wt. %, from 13 to 16.2 wt. %, from 13 to 16 wt. %, from 13 to 15.5 wt. %, from 13 to 15 wt. %, from 13.5 to 16 wt. %, from 13.5 to 15.5 wt. %, from 14 to 16.2 wt. %, from 14 to 16 wt. %, from 14 to 15.5 wt. %, or from 14 to 15 wt. %. Other appropriate ranges for the average thiol sulfur content are readily apparent from this disclosure.

In an embodiment, the sulfur-containing compounds of the polythiol composition can be characterized by the weight percentage of intermolecular sulfide compounds (having a —S— group) that often falls within a range from 2 wt. % to 90 wt. %. These percentages are based on the total sulfur-containing compounds of the composition, regardless of the number of thiol and/or sulfide groups. In certain embodiments, the sulfur-containing compounds of the polythiol composition can have a minimum weight percentage of intermolecular sulfide compounds of 2, 3, 5, 7, or 10 wt. %; additionally or alternatively, a maximum weight percentage of 90, 80, 70, 60, or 50 wt. %. Generally, the sulfur-containing compounds of the polythiol composition can have an amount of intermolecular sulfide compounds in a range from any minimum weight percentage to any maximum weight percentage disclosed herein. Therefore, suitable non-limiting ranges for the amount of intermolecular sulfide compounds present in the sulfur-containing compounds of the polythiol composition can include the following ranges: from 2 to 90 wt. %, from 2 to 70 wt. %, from 2 to 60 wt. %, from 2 to 50 wt. %, from 5 to 90 wt. %, from 5 to 70 wt. %, from 5 to 60 wt. %, from 5 to 50 wt. %, from 10 to 90 wt. %, from 10 to 80 wt. %, from 10 to 70 wt. %, from 10 to 60 wt. %, or from 10 to 50 wt. %. In some embodiments disclosed herein, a small percentage of the sulfur-containing compounds (e.g., less than 40 wt. %, less than 35 wt. %, less than 30 wt. %, etc.) of the polythiol compositions can be intermolecular sulfide compounds. Other appropriate ranges for the amount of intermolecular sulfide compounds are readily apparent from this disclosure.

In an embodiment, the sulfur-containing compounds of the polythiol compositions can have a weight percentage of compounds with a thiol sulfur group, but no sulfide sulfur groups, that often can fall within a range from 30 wt. % to 95 wt. %. These percentages are based on the total sulfur-containing compounds of the composition, regardless of the number of thiol and/or sulfide groups. In certain embodiments, the sulfur-containing compounds of the polythiol composition can have a minimum weight percentage of compounds with a thiol sulfur group (but no sulfide sulfur groups) of 30, 35, 40, 45, or 50 wt. %; additionally or alternatively, a maximum weight percentage of 95, 90, 85, or 80 wt. %. Generally, the sulfur-containing compounds of the polythiol composition can have a weight percentage of compounds with a thiol sulfur group (but no sulfide sulfur groups) in a range from any minimum weight percentage to any maximum weight percentage disclosed herein. Therefore, suitable non-limiting ranges for the weight percentage of compounds with a thiol sulfur group (but no sulfide sulfur groups) in the sulfur-containing compounds of the polythiol composition can include the following ranges: from 30 to 90 wt. %, from 30 to 85 wt. %, from 30 to 80 wt. %, from 35 to 95 wt. %, from 35 to 90 wt. %, from 35 to 85 wt. %, from 35 to 80 wt. %, from 40 to 95 wt. %, from 40 to 90 wt. %, from 40 to 85 wt. %, from 40 to 80 wt. %, from 45 to 90 wt. %, from 45 to 85 wt. %, from 50 to 95 wt. %, from 50 to 85 wt. %, or from 50 to 80 wt. %. In some embodiments disclosed herein, a majority of the sulfur-containing compounds (e.g., greater than 50 wt. %, greater than 60 wt. %, greater than 70 wt. %, etc.) of the polythiol composition can be compounds with a thiol sulfur group, but no sulfide sulfur groups. Other appropriate ranges for the total amount of compounds with a thiol group, but no sulfide sulfur groups, are readily apparent from this disclosure.

Consistent with particular embodiments of this invention, the sulfur-containing compounds of the polythiol compositions can be further characterized by the thiol or mercaptan equivalent weight (or SHEW) of the composition. The SHEW is based on the total sulfur-containing compounds of the composition, regardless of the number of thiol and/or sulfide groups. For instance, the minimum SHEW of sulfur-containing compounds of the composition can be 198, 199, 200, or 205 g/eq; additionally or alternatively, the maximum SHEW of sulfur-containing compounds of the composition can be 300, 275, 250, or 225 g/eq. Generally, the sulfur-containing compounds of the polythiol composition can have a SHEW in a range from any minimum SHEW to any maximum SHEW disclosed herein. Therefore, suitable non-limiting ranges for the SHEW of the sulfur-containing compounds can include the following ranges: from 198 to 300, from 198 to 275, from 198 to 250, from 198 to 225, from 199 to 250, from 200 to 300, from 200 to 275, from 200 to 250, from 200 to 225, from 205 to 275, from 205 to 250, or from 205 to 225 g/eq. Other appropriate ranges for the SHEW are readily apparent from this disclosure.

In an embodiment, the sulfur-containing compounds of the polythiol compositions can be further characterized by the average thiol functionality of the sulfur-containing compounds of the composition. The average thiol functionality is based on the total sulfur-containing compounds of the composition, regardless of the number of thiol and/or sulfide groups. For instance, the minimum average thiol functionality of sulfur-containing compounds of the composition can be 4.05, 4.1, 4.15, or 4.2; additionally or alternatively, the maximum thiol functionality of sulfur-containing compounds of the composition can be 6, 5.5, 5, or 4.9 g/eq. Generally, the sulfur-containing compounds of the polythiol composition can have an average thiol functionality in a range from any minimum thiol functionality to any maximum thiol functionality disclosed herein. Therefore, suitable non-limiting ranges for the average thiol functionality of the sulfur-containing compounds can include the following ranges: from 4.05 to 6, from 4.05 to 5.5, from 4.05 to 5, from 4.05 to 4.9, from 4.1 to 6, from 4.1 to 5, from 4.1 to 4.9, from 4.2 to 5.5, from 4.2 to 5, or from 4.2 to 4.9. Other appropriate ranges for the average thiol functionality are readily apparent from this disclosure.

In some embodiments, the polythiol compositions disclosed herein can be produced by any process described herein. Additional information on processes for producing such polythiol compositions is provided herein.

Processes for Producing Polythiol Compositions

In accordance with certain embodiments of this invention, a process for producing a polythiol composition can comprise (1) contacting a compound having formula (A):

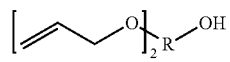

with a compound having formula (B):

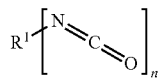

to form a reaction mixture comprising a polycarbamate; and (2) contacting the polycarbamate, $H_2S$, and an optional phosphite compound to form the polythiol composition. Generally, the molar ratio of $H_2S$ to carbon-carbon double bonds of the polycarbamate can be in a range from 2:1 to 500:1. The polythiol composition can comprise sulfur-containing compounds having formula (I):

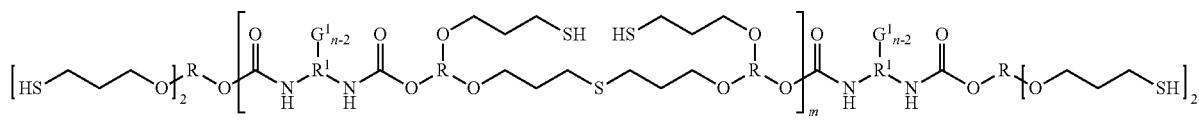

Generally, the features of the process (e.g., the use of the phosphite compound, the hydrogen sulfide to carbon-carbon double bond ratio, the components of and/or features of the polythiol composition, the conditions under which the polycarbamate is formed, the conditions under which the polythiol composition is formed, $G^1$, R, $R^1$, n, m, an average value of m in the composition, among other process features) are independently described herein and these features can be combined in any combination to further describe the disclosed process. In formula (I), $G^1$ can have formula (II):

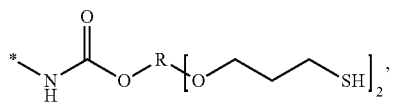

each R independently can be any $C_3$ to $C_{15}$ hydrocarbon group disclosed herein, each $R^1$ independently can be any $C_1$ to $C_{30}$ hydrocarbon group disclosed herein, n can be any integer greater than or equal to 2 disclosed herein, and m can be any integer from 0 to 6 disclosed herein. In an embodiment, the average value of m in the composition can range from greater than 0 to 3. It should be noted that while m of the sulfur-containing compound having formula (I) is an integer, the average value of m for the sulfur-containing compounds of the polythiol composition can be any positive number from greater than 0 to 3, or in any other range disclosed herein.

Consistent with embodiments of this invention, a step of the process for producing a polythiol composition can comprise contacting a compound having formula (A) with a compound having formula (B) to form a reaction mixture comprising a polycarbamate. In some embodiments, for instance, the polycarbamate can comprise compounds having formula (C):

(C)

[diagram of formula C]

wherein G =

[diagram]

In formula (C), each R, $R^1$, and n independently can be the same as described herein for sulfur-containing compounds having formula (I). For example, $R^1$ in formula (C) can be any $C_1$-$C_{30}$ hydrocarbon group, $C_1$ to $C_{10}$ hydrocarbon group, non-olefinic $C_1$-$C_{30}$ hydrocarbon group, non-olefinic $C_1$ to $C_{10}$ hydrocarbon group, $C_1$ to $C_{30}$ alkane group, $C_1$ to $C_{10}$ alkane group, aliphatic $C_4$ to $C_{30}$ cyclohydrocarbon group, aliphatic $C_6$ to $C_{12}$ cyclohydrocarbon group, $C_4$ to $C_{30}$ cycloalkane group, $C_6$ to $C_{12}$ cycloalkane group, $C_6$ to $C_{30}$ aromatic group, or $C_6$ to $C_{12}$ aromatic group that conforms to the rules of chemical valence, and such groups can be substituted or unsubstituted, as described herein. Also in formula (C), for example, each R can be the same or different and can be any $C_3$-$C_{15}$ hydrocarbon group, $C_3$ to $C_{10}$ hydrocarbon group, non-olefinic $C_3$-$C_{15}$ hydrocarbon group, non-olefinic $C_3$ to $C_{10}$ hydrocarbon group, $C_3$ to $C_{15}$ alkane group, $C_3$ to $C_{10}$ alkane group, $C_4$ to $C_{15}$ cycloalkane group, or $C_6$ to $C_{12}$ cycloalkane group that conforms to the rules of chemical valence, and such groups can be substituted or unsubstituted, as described herein. Also in formula (C), for example, the integer n can be greater than or equal to 2, from 2 to 4, from 2 to 3, equal to 2, or equal to 3.

In other embodiments, wherein the integer n in formula (C) can be equal to 2, the polycarbamate can comprise compounds having formula (D):

(D)

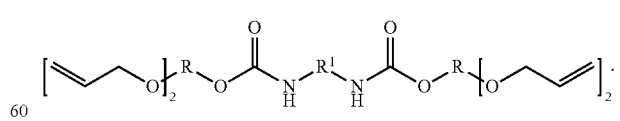

In formula (D), each R and $R^1$ independently can be the same as described herein for formula (I) or for formula (C).

In particular embodiments contemplated herein, the polycarbamate can comprise the following compound:

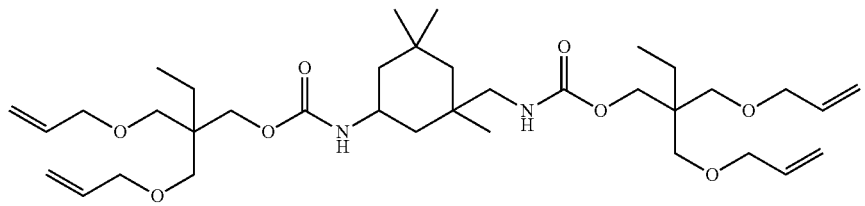

The R moiety in the compound having formula (A), which is contacted with a compound having formula (B) to form a reaction mixture comprising a polycarbamate, can be any R group disclosed herein for formula (I). For example, in formula (A), R can be any $C_3$-$C_{15}$ hydrocarbon group, $C_3$ to $C_{10}$ hydrocarbon group, non-olefinic $C_3$-$C_{15}$ hydrocarbon group, non-olefinic $C_3$ to $C_{10}$ hydrocarbon group, $C_3$ to $C_{15}$ alkane group, $C_3$ to $C_{10}$ alkane group, $C_4$ to $C_{15}$ cycloalkane group, or $C_6$ to $C_{12}$ cycloalkane group that conforms to the rules of chemical valence, and such groups can be substituted or unsubstituted, as described herein.

Representative and non-limiting examples of compounds having formula (A) can include bis(allyl ether) of glycerol, bis(allyl ether) of trimethylolpropane, bis(allyl ether) of trimethylolethane, bis(allyl ether) of trimethylolmethane, and the like, as well as combinations thereof. In an embodiment, the compound having formula (A) can comprise bis(allyl ether) of glycerol; alternatively, bis(allyl ether) of trimethylolpropane; alternatively, bis(allyl ether) of trimethylolethane; or alternatively, bis(allyl ether) of trimethylolmethane. Thus, in particular embodiments contemplated herein, the compound having formula (A) can comprise the following compound:

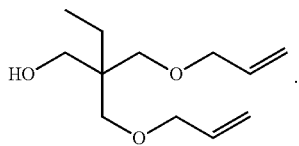

The $R^1$ moiety and the integer n in the compound having formula (B) can be any $R^1$ group and integer n disclosed herein for formula (I). For example, in formula (B), $R^1$ can be any $C_1$-$C_{30}$ hydrocarbon group, $C_1$ to $C_{10}$ hydrocarbon group, non-olefinic $C_1$-$C_{30}$ hydrocarbon group, non-olefinic $C_1$ to $C_{10}$ hydrocarbon group, $C_1$ to $C_{30}$ alkane group, $C_1$ to $C_{10}$ alkane group, aliphatic $C_4$ to $C_{30}$ cyclohydrocarbon group, aliphatic $C_6$ to $C_{12}$ cyclohydrocarbon group, $C_4$ to $C_{30}$ cycloalkane group, $C_6$ to $C_{12}$ cycloalkane group, $C_6$ to $C_{30}$ aromatic group, or $C_6$ to $C_{12}$ aromatic group that conforms to the rules of chemical valence, and such groups can be substituted or unsubstituted, as described herein. Also in formula (B), for example, the integer n can be greater than or equal to 2, from 2 to 4, from 2 to 3, equal to 2, or equal to 3.

Generally, the compound having formula (B) can comprise any suitable isocyanate, for instance, an aromatic isocyanate, an aliphatic isocyanate, a cycloaliphatic isocyanate, and the like, as well as mixtures or combinations thereof. Representative and non-limiting examples of compounds having formula (B) can include isophorone diisocyanate, 1,6-hexamethylene diisocyanate (1,6-hexane diisocyanate, HDI), 1,6-hexane diisocyanate trimer (there are two types, but both have three isocyanate groups), 1,3-bis(isocyanato-methyl) cyclohexane, 1,4-bis(isocyanato-methyl) cyclohexane, 4,4'-dicyclohexylmethane diisocyanate (HDMI), 1,4-phenylene diisocyanate (PPDI), 1,3-(isocyanatopropyl)benzene, 4,4'-diphenylmethane diisocyanate (MDI), polymeric diphenylmethane diisocyanate (PMDI, PPI, PAPI), 2,4-toluene diisocyanate (TDI), 1,5-diisocyanato naphthalene, and the like, as well as combinations thereof. The compound having formula (B) is not limited to the representative compounds disclosed above; other suitable isocyanates are disclosed in U.S. Pat. No. 8,003,748, incorporated herein by reference in its entirety.

In particular embodiments contemplated herein, the compound having formula (B) can comprise the following compound:

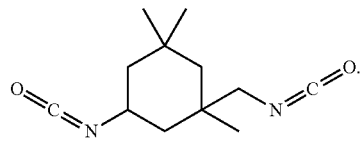 [SMILES: CC1(C)CC(N=C=O)CC(C)(CN=C=O)C1]

In the processes disclosed herein, the minimum equivalent ratio of the compound having formula (A) to the compound having formula (B) can be 0.8:1, 0.85:1, 0.9:1, 0.95:1, or 0.97:1; additionally or alternatively, the maximum equivalent ratio of the compound having formula (A) to the compound having formula (B) can be 2:1, 1.5:1, 1.25:1, 1.15:1, or 1.1:1. Generally, the equivalent ratio of the compound having formula (A) to the compound having formula (B) can range from any minimum equivalent ratio disclosed herein to any maximum equivalent ratio disclosed herein. Therefore, suitable ranges for the equivalent ratio of the compound having formula (A) to the compound having formula (B) can include, but are not limited to, the following ranges: from 0.8:1 to 2:1, from 0.85:1 to 1.5:1, from 0.9:1 to 2:1, from 0.9:1 to 1.5:1, from 0.9:1 to 1.25:1, from 0.9:1 to 1.1:1, from 0.95:1 to 1.5:1, from 0.95:1 to 1.25:1, from 0.95:1 to 1.15:1, from 0.95:1 to 1.1:1, from 0.97:1 to 1.5:1, from 0.97:1 to 1.15:1, or from 0.97:1 to 1.1:1. Other appropriate ranges for the equivalent ratio of the compound having formula (A) to the compound having formula (B) are readily apparent from this disclosure.

In an embodiment, the step of contacting the compound having formula (A) and the compound having formula (B) to form a reaction mixture comprising a polycarbamate can include additional unrecited materials (e.g., a solvent). In other embodiments, this step can consist essentially of contacting the compound having formula (A) with the compound having formula (B) to form a reaction mixture comprising a polycarbamate, or alternatively, consist of contacting the compound having formula (A) with the compound having formula (B) to form a reaction mixture comprising a polycarbamate.

Forming the reaction mixture comprising a polycarbamate can be conducted at a variety of temperatures, pressures, and time periods. In an embodiment, the forming of the reaction mixture comprising a polycarbamate can be conducted at a temperature in a range from −30° C. to 150° C.; alternatively, from −20° C. to 130° C.; alternatively, from −10° C. to 100° C.; alternatively, from −5° C. to 80° C.; alternatively, from 0° C. to 60° C.; or alternatively, from 10° C. to 45° C. These temperature ranges also are meant to encompass circumstances where the forming of the reaction mixture comprising a polycarbamate can be conducted at a series of different temperatures, instead of at a single fixed temperature, falling within the respective ranges.

The forming of the reaction mixture comprising a polycarbamate can be conducted at a total reactor pressure in a range from 30 to 1500 psig, such as, for example, from 50 to 1500 psig. In some embodiments, the forming of the reaction mixture comprising a polycarbamate can be conducted at total reactor pressure in a range from 50 to 1500 psig; alternatively, from 50 to 1000 psig; alternatively, from 50 to 750 psig; alternatively, from 50 to 500 psig; or alternatively, from 100 to 500 psig.

The time to form the reaction mixture comprising a polycarbamate is not limited to any particular range. That is, the time period in which the reaction mixture comprising a polycarbamate can be formed can be a period of time ranging from as little as about 1-30 seconds to as long as about 1-24 hours, or more. In some embodiments, the time period in which the reaction mixture comprising a polycarbamate can be formed can depend on many variables, but in some embodiments, the time period can be in a range from 1 minute to 8 hours, such as, for example, from 2 minutes to 6 hours, from 5 minutes to 5 hours, from 10 minutes to 4 hours, or from 15 minutes to 3 hours.

In an embodiment, the step of contacting the polycarbamate, $H_2S$, and an optional phosphite compound to form the polythiol composition can comprise contacting the polycarbamate, $H_2S$, the optional phosphite compound, and additional unrecited materials (e.g., a solvent). In other embodiments, the step of contacting the polycarbamate, $H_2S$, and an optional phosphite compound to form the polythiol composition can consist essentially of contacting the polycarbamate, $H_2S$, and the optional phosphite compound or, alternatively, consist of contacting the polycarbamate, $H_2S$, and the optional phosphite compound. Additional materials or features can be employed in the step of contacting the polycarbamate, $H_2S$, and an optional phosphite compound to form the polythiol composition. For instance, the formation of the polythiol composition can occur in the presence of ultraviolet light, discussed further herein. Moreover, it is contemplated that when the processes for producing polythiol compositions utilize a phosphite compound, the processes can employ more than one phosphite compound.

In the processes disclosed herein, the minimum molar ratio of $H_2S$ to carbon-carbon double bonds of the polycarbamate can be 2:1, 3:1, 5:1, or 10:1; additionally or alternatively, the maximum molar ratio of $H_2S$ to carbon-carbon double bonds of the polycarbamate can be 500:1, 250:1, 150:1, 100:1, or 50:1. Generally, the molar ratio of $H_2S$ to carbon-carbon double bonds of the polycarbamate can range from any minimum molar ratio disclosed herein to any maximum molar ratio disclosed herein. Therefore, suitable ranges for the ratio of $H_2S$ to carbon-carbon double bonds of the polycarbamate can include, but are not limited to, the following ranges: from 2:1 to 500:1, from 2:1 to 250:1, from 2:1 to 100:1, from 2:1 to 50:1, from 3:1 to 250:1, from 3:1 to 150:1, from 3:1 to 100:1, from 5:1 to 500:1, from 5:1 to 150:1, from 5:1 to 50:1, from 10:1 to 250:1, from 10:1 to 150:1, from 10:1 to 100:1, or from 10:1 to 50:1. Other appropriate ranges for the molar ratio of $H_2S$ to carbon-carbon double bonds of the polycarbamate are readily apparent from this disclosure.

When the phosphite compound is used in the processes disclosed herein, the minimum molar ratio of the phosphite compound to carbon-carbon double bonds of the polycarbamate can be 0.0005:1, 0.001:1, 0.005:1, or 0.006:1; additionally or alternatively, the maximum molar ratio of the phosphite compound to carbon-carbon double bonds of the polycarbamate can be 0.1:1, 0.075:1, or 0.05:1. Generally, the molar ratio of the phosphite compound to carbon-carbon double bonds of the polycarbamate can range from any minimum molar ratio disclosed herein to any maximum molar ratio disclosed herein. Therefore, suitable ranges for the molar ratio of the phosphite compound to carbon-carbon double bonds of the polycarbamate can include, but are not limited to, the following: from 0.0005:1 to 0.1:1, from 0.0005:1 to 0.075:1, from 0.0005:1 to 0.05:1, from 0.001:1 to 0.1:1, from 0.001:1 to 0.075:1:1, from 0.001:1 to 0.05:1, from 0.005:1 to 0.1:1, from 0.005:1 to 0.05:1, from 0.006:1 to 0.1:1, from 0.006:1 to 0.05:1, from 0.008:1 to 0.05:1, from 0.008:1 to 0.04:1, from 0.01:1 to 0.1:1, or from 0.01:1 to 0.05:1. Other appropriate ranges for the molar ratio of phosphite compound to carbon-carbon double bonds of the polycarbamate are readily apparent from this disclosure.

The step comprising contacting the polycarbamate, $H_2S$, and an optional phosphite compound to form the polythiol composition can be conducted at a variety of temperatures, pressures, and time periods. In an embodiment, the forming of a polythiol composition can be conducted at a temperature in a range from −30° C. to 150° C.; alternatively, from −20° C. to 130° C.; alternatively, from −10° C. to 100° C.; alternatively, from −5° C. to 80° C.; alternatively, from 0° C. to 60° C.; or alternatively, from 10° C. to 45° C. These temperature ranges also are meant to encompass circumstances where the forming of a polythiol composition can be conducted at a series of different temperatures, instead of at a single fixed temperature, falling within the respective ranges.

The forming of a polythiol composition can be conducted at a total reactor pressure in a range from 30 to 1500 psig, such as, for example, from 50 to 1500 psig. In some embodiments, the forming of a polythiol composition can be conducted at total reactor pressure in a range from 50 to 1500 psig; alternatively, from 50 to 1000 psig; alternatively, from 50 to 750 psig; alternatively, from 50 to 500 psig; or alternatively, from 100 to 500 psig.

The time to form the polythiol composition is not limited to any particular range. That is, the time period in which the polythiol can be formed can be conducted, for example, in a time period ranging from as little as about 1-30 seconds to as long as about 1-24 hours, or more. In some embodiments, the time period in which the polythiol can be formed can depend on many variables, but in some embodiments, the time period in which the polythiol can be formed can be in a range from 1 minute to 8 hours, such as, for example, from 2 minutes to 6 hours, from 5 minutes to 5 hours, from 10 minutes to 4 hours, or from 15 minutes to 3 hours.

In embodiments of this invention, once the polycarbamate, $H_2S$, and the phosphite compound (if used) are contacted, the polythiol composition can be formed in the presence of electromagnetic radiation. For instance, the polythiol composition can be formed in the presence of ultraviolet light. Additionally or alternatively, the polythiol composition can be formed by light photolysis initiation of a free radical initiator. Additionally or alternatively, the polythiol composition can be formed under conditions suitable for the thermal decomposition of a free radical initiator. Additionally, a photoinitiator can be utilized in conjunction with ultraviolet light or light photolysis initiation of a free radical initiator. Free radicals, therefore, can be generated in situ by a suitable energy source, or can be generated by the thermal decomposition of a free radical initiator, or by a combination of these sources. The polythiol composition can be formed in the presence of free radicals from any one of aforementioned sources, including combinations thereof, but is not limited to free radicals generated only by these means.

When the polythiol composition is formed in the presence of ultraviolet light, ultraviolet light in the range, for example, from 172 to 450 nm, from 172 to 380 nm, or from 172 to 320 nm, can be employed. Ultraviolet light can be supplied from ultraviolet lamps, but other sources of ultraviolet light can be employed, and are to be considered within the scope of the present invention.

The free radical initiator can be any free radical initiator capable of forming free radicals under thermal decomposition or light photolysis. For example, the free radical initiator employed for the formation of the polythiol composition can comprise a —N=N— group, a —O—O— group, or combinations thereof; alternatively, a —N=N— group; or alternatively, a —O—O— group. Free radical initiators, therefore, can include, but are not limited to, peroxy compounds, organic azo compounds, or combinations thereof; alternatively, peroxy compounds; or alternatively, organic azo compounds. Peroxy compounds which can be utilized can include peroxides, hydroperoxides, peroxyesters, diacylperoxides, and percarbonates; alternatively, peroxides; alternatively, hydroperoxides; alternatively, peroxyesters; alternatively, diacylperoxides; or alternatively, percarbonates. In an embodiment, the peroxide can be a dialkyl peroxide. In an embodiment, the hydroperoxide can be an alkyl hydroperoxide. In an embodiment, the peroxy ester can be an alkyl peroxyalkanoate, or alternatively, an alkyl peroxyarenoate. In an embodiment, the diacylperoxide can be a diaroyl peroxide, or alternatively, a diakoyl peroxide. In an embodiment, the percarbonate can be a dihydrocarbyl percarbonate; alternatively, a diarylpercarbonate; or alternatively, a dialkylpercarbonate. Generally, the hydrocarbon and/or alkane group(s) utilized in any peroxy compound can be a $C_1$ to $C_{30}$, $C_2$ to $C_{18}$, $C_2$ to $C_{10}$, or $C_2$ to $C_5$ hydrocarbon and/or alkane group(s). Generally, the arene group utilized in any peroxy compound can be a $C_6$ to $C_{30}$, $C_6$ to $C_{18}$, $C_6$ to $C_{15}$, or $C_6$ to $C_{10}$ arene group(s). Illustrative non-limiting examples of peroxy compounds which can be utilized can include, but are not limited to, diisobutyryl peroxide, 1-(2-ethylhexanoylperoxy)-1,3-dimethylbutyl peroxypivalate, cumylperoxyneodecanoate, 1,1,3,3-tetramethylbutyl peroxyneodecanoate, t-butyl peroxyneodecanoate, 1,1,3,3-tetramethylbutyl peroxypivalate, t-butyl peroxyneoheptanoate, t-amyl peroxypivalate, t-butyl peroxypivalate, di(3,5,5-trimethylhexanoyl) peroxide, dilauroyl peroxide, didecanoyl peroxide, 2,5-dimethyl-2,5-di(2-ethylhexanoylperoxy)hexane, 1,1,3,3-tetramethylbutyl peroxy 2-ethylhexanoate, t-amyl peroxy 2-ethylhexanoate, dibenzoyl peroxide, acetyl peroxide t-butyl peroxy 2-ethylhexanoate, t-butyl peroctanoate, t-butyl peroxydiethylacetate, t-butyl peroxyisobutyrate, t-butyl peroxy 3,5,5-trimethylhexanoate, t-butyl peroxyacetate, t-butyl peoxybenzoate, 2,4-dichlorobenzoyl peroxide, t-butylpermaleic acid, di-t-butyl diperphthalate, di(4-t-butylcyclohexyl) peroxydicarbonate, di(2-ethylhexyl) peroxydicarbonate, dibutyl peroxydicarbonate, dicetyl peroxydicarbonate, dimyristyl peroxydicarbonate, t-amylperoxy 2-ethylhexyl carbonate, t-butylperoxy isopropyl carbonate, t-butylperoxy 2-ethylhexyl carbonate, 1,1-di(t-butylperoxy) 3,5,5-trimethylcyclohexane, 2,2-di(4,4-di(t-butylperoxy)cyclohexyl)propane, 1,1-di(t-butylperoxy)cyclohexane, 2,2-di(t-butylperoxy)butane, di(t-amyl) peroxide, dicumyl peroxide, di(t-butylperoxyisopropyl) benzene, 2,5-dimethyl-2,5-di(t-butylperoxy)hexane, t-butyl cumyl peroxide, 2,5-dimethyl-2,5-di(t-butylperoxy)hexyne-3, di-t-butyl peroxide, 3,6,9-triethyl-3,6,9-trimethyl-1,4,7-triperoxoane, t-butyl hydroperoxide, methyl benzyl hydroperoxide, octylperbenzoate, methyl ethyl ketone peroxide, acetone peroxide, or combinations thereof.

Non-limiting examples of suitable azo compounds include α,α'-azo diisobutyronitrile (AIBN), azobenzene, azomethane, 2,2'-azodi(2-methylbutyronitrile), 2,2'-azobis(4-methoxy-2,4-dimethyl valeronitrile), dimethyl 2,2'-azobis(2-methylpropionate), 1,1'-azobis(cyclohexane-1-carbonitrile), 1-[(cyano-1-methylethyl)azo] formamide, 2,2'-azobis(N-cyclohexyl-2-methylpropionamide), 2,2'-azobis (2,4-dimethyl valeronitrile), 2,2'-azobis(2-methylbutyronitrile), 2,2'-azobis[N-(2-propenyl)-2-methylpropionamide], 2,2'-azobis(N-butyl-2-methylpropionamide), 2,2'-azobis {2-methyl-N-[1,1-bis (hydroxymethyl)-2-hydroxyethyl] propionamide, 2,2'-azobis[2-methyl-N-(2-hydroxyethyl)propionamide], 2,2'-azobis[2-(2-imidazolin-2-yl)propane], 2,2'-azobis {2-methyl-N-[2-(1-hydroxybutyl)] propionamide}, 2,2'-azobis(2-methylpropionitrile), 4,4'-azobis(4-cyanovaleric acid), 2,2'-azobis(2-methylpropane), 2,2'-azobis(2-methylpropionamidine)dihydrochloride, methylpropionitrile, azodicarboxamide, or combinations thereof.

Generally, the peroxide and azo compound free radical initiators that can be utilized in accordance with the present invention decompose under first order kinetics. Skilled artisans can readily find the first order kinetic parameters which can be utilized to describe the decomposition of a particular free radical catalyst from sources such as chemical suppliers, industry reference publications, and/or open literature publications. Under first order kinetics, the time required for a given fraction (or percentage) of the free radical initiator to decompose, at a specific temperature, into initiating species is independent of the concentration of the free radical. This phenomenon is often stated as a half-life; that is, the time in which one-half of the free radical initiator decomposes under specific conditions (e.g., temperature). According to the first order kinetics, the half-life of a free radical initiator is defined as the time it takes one-half of the initiator to decompose at a particular temperature. Using the available first order kinetic parameters for a particular free radical initiator, the concentration of the free radical initiator present in the reaction mixture can be determined at a particular time during the reaction based upon the knowledge of the amount of free radical initiator added to the reaction, the times at which additional (if any) free radical initiator is added to the reaction, and the temperature profile of the reaction.

When the polythiol composition is formed under conditions utilizing the thermal decomposition of a free radical initiator, the polythiol composition can be formed at a temperature within a temperature range of the 1 hour half-life of the free radical initiator. Alternatively, when the polythiol composition is formed under conditions utilizing the thermal decomposition of a free radical initiator, the polythiol composition can be formed using a free radical initiator having a half-life within a time range at the temperature utilized to form the polythiol composition. For example, the formation of the polythiol composition can be conducted at a temperature within ±25° C. of the 1 hour half-life of the free radical initiator. In other embodiments, the polythiol composition can be formed at a temperature within ±20° C. of the 1 hour half-life of the free radical initiator; alternatively, at a temperature within ±15° C. of the 1 hour half-life of the free radical initiator; alternatively, at a temperature within ±10° C. of the 1 hour half-life of the free radical initiator. In another embodiment, the polythiol composition can be formed using a free radical initiator having a half-life within a range from 0.1 to 10 hours at the temperature the polythiol composition is formed. Alternatively, the polythiol composition can be formed using a free radical initiator having a half-life ranging from 0.1 to 10 hours, from 0.25 to 4 hours, or from 0.5 to 2 hours, at the temperature the polythiol composition is formed. As above, in some embodiments of this invention, the polythiol composition can be formed at a temperature in a range from −30° C. to 150° C.; alternatively, from −20° C. to 130° C.; alternatively, from −10° C. to 100° C.; alternatively, from −5° C. to 80° C.; alternatively, from 0° C. to 60° C.; or alternatively, from 10° C. to 45° C.

Depending upon the particular free radical initiator, a free radical initiator can produce a different number of free radical reaction-initiating species per mole of free radical initiator; thus, the concentration of the free radical initiator can be stated in terms which describe the number of free radical reaction-initiating species generated per mole of free radical initiator. The term "equivalent" is often used to describe the number of reaction-initiating species produced per mole of free radical initiator. For example, one skilled in the art will readily recognize that di-t-butylperoxide can generate two free radical reaction-initiating species per mole of di-t-butylperoxide, while 2,5-bis(t-butylperoxy)-2,5-dimethylhexane can generate four free radical reaction-initiating species per mole of 2,5-bis(t-butylperoxy)-2,5-dimethylhexane.

In some embodiments, a photoinitiator can be utilized. Commercially available photoinitiators include, by way of example, Irgacure® 184 (1-hydroxy-cyclohexyl-phenyl-ketone), Irgacure® 500 (50% 1-hydroxy-cyclohexyl-phenyl-ketone and 50% benzophenone), Irgacure® 819 (Bis-(2,4, 6-trimethylbenzoyl)-phenylphosphineoxide), and Irgacure® 127 (2-hydroxy-1-{4-[4-(2-hydroxy-2-methyl-propionyl)-benzyl]-phenyl}-2-methyl-propan-1-one), all available from Ciba Specialty Chemicals, and Duracure 1173 (2-hydroxy-2-methyl-1-phenyl-1-propanone).

When a free radical initiator is present during the formation of the polythiol composition, the weight percentage of the free radical initiator, based on the weight of the polycarbamate, can be in a range from 0.05 to 10 wt. %, from 0.1 to 9 wt. %, from 0.2 to 5 wt. %, or from 0.1 to 2 wt. %. When a photoinitiator is present during the formation of the polythiol composition, the weight percentage of the photoinitiator, based on the weight of the polycarbamate, can be less than or equal to 5 wt. %, less than or equal to 3 wt. %, less than or equal to 2 wt. %, or less than or equal to 1.5 wt. %, less than or equal to 1.25 wt. %, less than or equal to 1 wt. %, less than or equal to 0.75 wt. %, or less than or equal to 0.5 wt. %, and typical non-limiting ranges can include from 0.01 to 5 wt. %, from 0.05 to 5 wt. %, from 0.5 to 3 wt. %, or from 1 to 4 wt. %. Other amounts of the free radical initiator and/or the photoinitiator can be employed depending on the specific process conditions used to form the polythiol composition (e.g., temperature, pressure, time) and the respective ratios of H$_2$S to polycarbamate and of phosphite compound to polycarbamate, amongst other factors. It is contemplated that more than one free radical initiator, more than one photoinitiator, or combinations of free radical initiator(s) and photoinitiator(s), can be employed.

In an embodiment, the polythiol composition can be formed in the absence of a solvent. However, in other embodiments, the polythiol can be formed in the presence of a solvent. Typically, when used, the solvent can be present in an amount up to 1,000 wt. %, based on the weight of the polycarbamate. Alternatively, the formation of the polythiol can be performed in the presence of a solvent in an amount up 750 wt. %, up to 500 wt. %, up to 250 wt. %, up to 200 wt. %, up to 150 wt. %, or up to 100 wt. %. When a solvent is utilized, the minimum amount of solvent utilized can be at least 5 wt. %, at least 10 wt. %, at least 25 wt. %, at least 50 wt. %, or at least 75 wt. %, based on the weight of the polycarbamate. Generally, the amount of solvent which can be utilized can range from any minimum amount of solvent disclosed herein to any maximum amount of solvent disclosed herein. In some non-limiting embodiments, the formation of the polythiol can be performed in the presence of a solvent in an amount of from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the polycarbamate. The solvent can be present during the formation of the polycarbamate, and remain present during the formation of the polythiol composition. Alternatively, the solvent can be added after the formation of the polycarbamate has been completed. Solvents which can be utilized as the solvent are described herein, and these solvents can be utilized without limitation in the processes described herein.

In the processes for producing a polythiol composition disclosed herein, it is contemplated that at least 60% of the carbon-carbon double bonds of the polycarbamate can react to form a sulfur-containing group in the polythiol composition. Often, at least 65% of the carbon-carbon double bonds of the polycarbamate can react to form a sulfur-containing group; alternatively, at least 70%; alternatively; at least 75%; alternatively, at least 80%; alternatively, at least 85%; alternatively, at least 90%; alternatively, at least 95%; alternatively, at least 98%; or alternatively, at least 99%.

Once formed, the polythiol composition, or specific fractions of the polythiol composition, can be purified and/or isolated and/or separated using suitable techniques which include, but are not limited to, evaporation, distillation, crystallization, extraction, washing, decanting, filtering, drying, including combinations of more than one of these techniques. In one embodiment, the process for producing a polythiol composition can further comprise a step of separating or removing at least a portion of the H$_2$S, of the phosphite compound (if used), of compounds having no sulfur atoms, or any combination thereof, from the polythiol composition. For instance, these materials can be separated or removed by distillation, by short path distillation, by wiped film evaporation, or by a combination of these techniques.

Consistent with embodiments of this invention, these processes for producing polythiol compositions can be used to produce any of the polythiol compositions disclosed herein.

Phosphite Compounds

Generally, the phosphite compound employed in certain processes for forming a polythiol composition disclosed herein can comprise, consist essentially of, or consist of, a compound having the formula:

In this formula, each $R^4$ independently can be a $C_1$-$C_{18}$ hydrocarbyl group; alternatively, a $C_1$-$C_{10}$ hydrocarbyl group; alternatively, a $C_1$-$C_5$ hydrocarbyl group; alternatively, a $C_1$-$C_{18}$ alkyl group; alternatively, a $C_1$-$C_{10}$ alkyl group; alternatively, a $C_1$-$C_5$ alkyl group; alternatively, a $C_6$-$C_{18}$ aryl group; or alternatively, a $C_6$-$C_{10}$ aryl group. Accordingly, each $R^4$ independently can be a methyl group, an ethyl group, a propyl group, a butyl group, a pentyl group, a hexyl group, a heptyl group, an octyl group, a nonyl group, or a decyl group; alternatively, $R^4$ can be a methyl group, an ethyl group, a propyl group, a butyl group, or a pentyl group; alternatively, $R^4$ can be a methyl group; alternatively, $R^4$ can be an ethyl group; alternatively, $R^4$ can be a propyl group; alternatively, $R^4$ can be a butyl group; alternatively, $R^4$ can be a pentyl group; alternatively, $R^4$ can be a hexyl group; alternatively, $R^4$ can be a heptyl group; alternatively, $R^4$ can be an octyl group; alternatively, $R^4$ can be a nonyl group; or alternatively, $R^4$ can be a decyl group. In some embodiments, each $R^4$ independently can be a phenyl group, a tolyl group, a xylyl group, or a naphthyl group; alternatively, a phenyl group, a tolyl group, or a xylyl group; alternatively, a phenyl group; alternatively, a tolyl group; alternatively, a xylyl group; or alternatively, a naphthyl group.

In accordance with an embodiment of this invention, the phosphite compound can comprise, consist essentially of, or consist of, a trialkylphosphite, or alternatively, a triarylphosphite. In accordance with another embodiment of this invention, the phosphite compound can comprise, consist essentially of, or consist of, trimethylphosphite, triethylphosphite, tributylphosphite, or combinations thereof. Yet, in accordance with another embodiment of this invention, the phosphite compound can comprise trimethylphosphite; alternatively, triethylphosphite; or alternatively, tributylphosphite. In another embodiment, the phosphite compound can comprise, consist essentially of, or consist of, triphenylphosphite.

Solvents

As described herein, the polythiol composition can be formed in the presence of a solvent. The solvent can comprise, consist essentially of, or consist of, a hydrocarbon, an aromatic hydrocarbon, a ketone, an ether, or combinations thereof. Hence, mixtures and/or combinations of solvents can be utilized in the processes of forming polythiol compositions disclosed herein.

In an embodiment, the solvent employed in forming the polythiol composition can comprise, consist essentially of, or consist of, a hydrocarbon solvent. Suitable hydrocarbon solvents can include, for example, aliphatic hydrocarbons, petroleum distillates, or combinations thereof. Aliphatic hydrocarbons which can be useful as the solvent include $C_3$ to $C_{20}$ aliphatic hydrocarbons; alternatively, $C_4$ to $C_{15}$ aliphatic hydrocarbons; or alternatively, $C_5$ to $C_{10}$ aliphatic hydrocarbons. The aliphatic hydrocarbons can be cyclic or acyclic, and/or can be linear or branched, unless otherwise specified.

Non-limiting examples of suitable acyclic aliphatic hydrocarbon solvents that can be utilized singly or in any combination include pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), decane (n-decane or a mixture of linear and branched $C_{10}$ acyclic aliphatic hydrocarbons), and combinations thereof; alternatively, pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), and combinations thereof; alternatively, hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons); alternatively, hexane (n-hexane or a mixture of linear and branched $C_6$ acyclic aliphatic hydrocarbons); alternatively, heptane (n-heptane or a mixture of linear and branched $C_7$ acyclic aliphatic hydrocarbons); or alternatively, octane (n-octane or a mixture of linear and branched $C_8$ acyclic aliphatic hydrocarbons).

In an embodiment, the solvent employed in forming the polythiol composition can comprise, consist essentially of, or consist of, an aromatic hydrocarbon solvent. Aromatic hydrocarbons can include $C_6$ to $C_{30}$ aromatic hydrocarbons; alternatively, $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

In an embodiment, the solvent employed in forming the polythiol composition can comprise, consist essentially of, or consist of, a ketone solvent, an ether solvent, or combinations thereof; alternatively, a ketone solvent; or alternatively, an ether solvent. Suitable ketones or ethers include $C_2$ to $C_{20}$ ketones or ethers; alternatively, $C_2$ to $C_{10}$ ketones or ethers; or alternatively, $C_2$ to $C_5$ ketones or ethers. Non-limiting examples of suitable ketone solvents can include acetone, ethyl methyl ketone, and combinations thereof. Suitable ether solvents can be cyclic or acyclic, non-limiting examples of which can include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

Articles

The polythiol compositions disclosed herein can be used as curing agents for various applications, such as epoxy and urethane coatings, paints, adhesives, binders, sealants, optical resins, laminates, and other end-use articles. For instance, the polythiol compositions and formulations produced therefrom (e.g., curing agent formulations) can be used with metal (e.g., aluminum, steel, copper, etc.), wood, glass, ceramic, and plastic substrates, including combinations of these substrates.

Formulations containing the polythiol compositions can contain other additives or components depending upon the desired properties and end-use application. These additives or components can include, but are not limited to, catalysts, solvents/diluents, plasticizers, fillers, fibers, pigments/colorants, pigment dispersing agents, flow modifiers, surface modifiers, antioxidants or stabilizers, or combinations thereof.

It is contemplated that formulations, coatings, paints, adhesives, binders, sealants, optical resins, laminates, and other articles of manufacture that contain and/or are produced from the polythiol compositions disclosed herein can have superior weatherability and toughness as compared to that of similar materials that contain polythiol compositions produced by other processes.

The polythiol compositions disclosed herein can also be used as reactants or intermediates in the preparation of other articles, for example as chain transfer agents to produce polymers.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

The following materials (and their respective abbreviations) were used in the examples that follow: isophorone diisocyanate (IPDI), bis(allyl ether) of trimethylolpropane or trimethylolpropane diallyl ether (TMP-DAE), dibutyltin dilaurate (catalyst), triethylphosphite (TEP), and photoinitiator available from CIBA (Irgacure® 500). An illustrative synthesis scheme for the following examples is provided below.

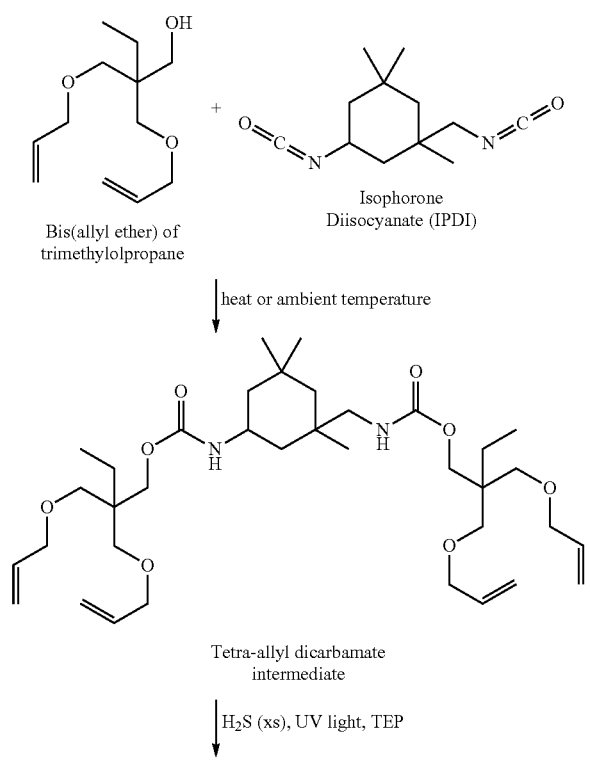

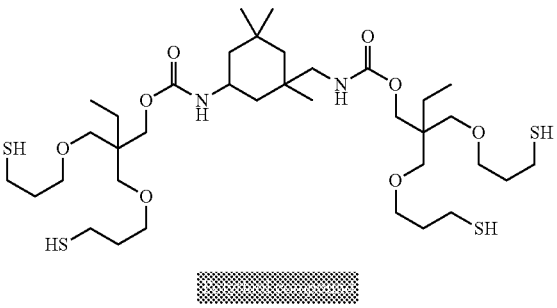

Autoclaves (1.5-L and 5-L) were used for the UV thiolations with $H_2S$. Raman spectroscopy was conducted in situ during the reaction and in a vial sample on the starting materials and final product, using a Kaiser RXN-2 Raman Spectrometer. The in situ Raman was conducted in the 1.5-L autoclave using a ¼-inch probe with a quartz window, and in the 5-L autoclave using a ½-inch probe. The respective reactors had a quartz lamp well mounted horizontal to an off-set stir shaft, and were equipped with a thermowell, cooling coils, a charge port, a sample port, and a bottom drain valve. Reactors were pressure checked with nitrogen prior to each experiment. Operating pressures were generally around 350 psig. The reactor contents were heated and controlled by setting the external circulating bath at the desired temperature of about 25° C.

The reactant materials were allowed to mix for 15 to 30 minutes before the ultraviolet lamp was turned on. The ultraviolet lamp (100 watts) typically required from 3 to 7 minutes to reach full power. When the conversion of carbon-carbon double bonds was complete or the desired reaction time was reached, the ultraviolet lamp was turned off. The $H_2S$ was then slowly vented from the reactor. The reactor was purged with nitrogen and the contents were drained via a bottom drain valve. The reaction product was placed in a rotoevaporator at 60° C. and low vacuum (approximately 10 torr) to remove additional residual $H_2S$ and other light materials (e.g., solvent). A Pope wiped-film evaporator (WFE) was used in some examples to further isolate the sulfur-containing compounds of the polythiol composition by removal of residual solvent, partial reaction products and/or phosphites. Typical conditions for the WFE were a wall temperature of 100° C. to 130° C. and a pressure of 1 torr to 10 torr.

Weight percentage of thiol sulfur (% SH) was determined by iodine titration. In a 250-mL Erlenmeyer flask, 0.1-0.3 grams of a sample were weighed to four decimal places. Next, 50 mL of a 2-propanol/dichloromethane (50/50) solution was added to the flask, and stirred to dissolve the sample. If the sample was colored, 1 mL of pyridine was added just before titration. While stirring, 0.1 N aqueous iodine solution was added via 50 mL burette until a pale yellow color persisted for at least 20 seconds. Duplicate or triplicate samples were run.

Weight percentage of total sulfur (% Total Sulfur) was determined by x-ray analysis using a Horiba SLFA-20 Total Sulfur-in-Oil Analyzer. FT-IR analysis was conducted using a Perkin-Elmer Spectrum One FT-IR Spectrometer. Viscosities were determined at ambient temperature using a Brookfield R/S+Rheometer with a cone and plate configuration.

Example 1

Producing a Polycarbamate from Isophorone Diisocyanate (IPDI) and Trimethylolpropane Diallyl Ether (TMP-DAE)

Example 1 was conducted at a 1:1 equivalent ratio (a 2:1 molar ratio) of trimethylolpropane diallyl ether (TMP-DAE) to isophorone diisocyanate (IPDI). IPDI (109.4 g) and TMP-DAE (211.5 g) were charged into a stirred reactor vessel. Approximately 0.01 g of catalyst (dibutyltin dilaurate) was added and the reaction mixture heated exothermically from 19.8 to 97.4° C. before beginning to cool. After 1.5 hr, the temperature was controlled at 55° C. and another 0.01 g catalyst charge was made, but no further exotherm was seen. Two hours later, another catalyst charge of 0.24 g was added to complete the reaction. A significant increase in viscosity was seen at this time, although the reaction mixture was still clear and nearly colorless. A sample was taken for FT-IR and the mixture was kept under nitrogen at ambient temperature for four days. A sample taken after 5.5 hours also showed that the reaction was essentially complete after a 5.5 hour reaction time. The following week, the mixture was heated to about 49° C. over the course of 2 hr to reduce the viscosity, and then discharged into a bottle. The isolated yield of the reaction mixture containing the polycarbamate was 89%. The product was highly viscous, clear, and nearly colorless. A final sample of the product was taken for FT-IR analysis, and the FT-IR spectrum showed the complete absence of the isocyanate peak around 2250 cm$^{-1}$ and the formation of a strong urethane carbonyl peak at 1699 cm$^{-1}$.

TABLE I

Reaction conditions for Example 2.

| Time (min) | Bath Temp (° C.) | Reaction Temp (° C.) | Reaction Pressure (psig) | Lamp Amps | Lamp Volts | Run Time (min) | Comments |
|---|---|---|---|---|---|---|---|
| 0 | 23.2 | 22.8 | 326 | — | — | — | H$_2$S added |
| 15 | 25.0 | 24.2 | 334 | 1.3 | 32.4 | 0 | Lamp on, Raman on |
| 21 | 25.0 | 26.7 | 350 | 1.1 | 87.8 | 6 | Lamp full power |
| 35 | 25.0 | 26.7 | 350 | 1.1 | 87.6 | 20 | Lamp off, vent H$_2$S |

The reaction mixture was subjected to rotoevaporation to remove volatile components including the acetone solvent. The resulting polythiol product after rotary evaporation was clear and colorless, but highly viscous. Consumption of the olefinic groups (1646 cm$^{-1}$) was apparent by FT-IR. Raman spectroscopy showed rapid and complete consumption of the olefinic bonds (1640-1650 cm$^{-1}$) within about 15 minutes. A large Raman spectral thiol peak also appeared at 2550 cm$^{-1}$ and an organosulfur (thiol and/or sulfide) peak also appeared at 650 cm$^{-1}$.

Mercaptan sulfur (iodine) titration and x-ray total sulfur analysis (Horiba) showed that the polythiol composition contained about 41 wt. % thiol product (structure shown below) and 59 wt. % monosulfide dimer, assuming no higher oligomers and no residual olefin groups (reasonable assumptions based on the Raman data) were present. The composition had an average molecular weight of 1109 and an average functionality of 4.86. Additional data on the polythiol composition of Example 2 is shown in Table IV.

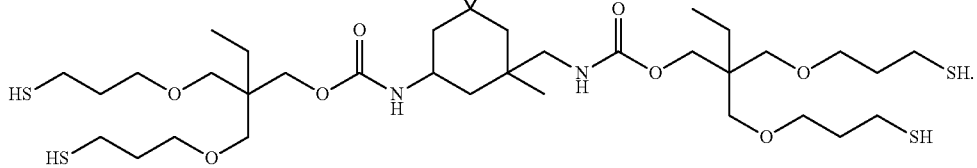

Example 2

Examples 3-6

Polythiol Composition Produced from a Polycarbamate and H$_2$S

A portion (69.7 g) of the polycarbamate intermediate from Example 1 was thiolated with H$_2$S (50:1 molar ratio of H$_2$S to carbon-carbon double bonds) in the 1.5-L autoclave at ambient temperature (~25° C.) with a 100-watt UV lamp under nitrogen. Acetone (100 mL) was used as a diluent, and triethylphosphite (TEP, 0.894 g) and a photoinitiator (Irgacure® 500, 0.193 g) were also used. The reaction was monitored for olefin consumption and thiol formation by Raman spectroscopy. The reaction was complete in less than 15-20 minutes. A final sample was taken for FT-IR and Raman analysis. Table I summarizes certain reaction conditions for Example 2.

Producing Polycarbamates from Isophorone Diisocyanate (IPDI) and Trimethylolpropane Diallyl Ether (TMP-DAE)

Examples 3-6 were conducted in a 1-L jacketed glass reactor equipped with a mechanical stirrer, condenser, and addition funnel. The TMP-DAE and catalyst (dibutyltin dilaurate) were added to the reactor and heated to 70° C. The IPDI was added slowly to control the strong reaction exotherm. Once the IPDI addition was complete, a sample was taken for FT-IR analysis. The reaction temperature was maintained at 70° C. and samples were taken periodically for FT-IR to monitor the disappearance of the IPDI (isocyanate peak at around 2250 cm$^{-1}$). Table II summarizes certain process conditions for Examples 3-6.

TABLE II

Reaction conditions for Examples 3-6.

| Example | TMP-DAE (g) | Catalyst (g) | IPDI (g) | IPDI Addition Time (hr) | Reaction Temp Range (° C.) | Total Reaction Time (hr) |
|---|---|---|---|---|---|---|
| 3 | 211 | 0.32 | 109 | 1.72 | 69-76 | 15.05 |
| 4 | 395 | 0.60 | 205 | 1.40 | 69-78 | 10.50 |
| 5 | 395 | 0.61 | 205 | 1.00 | 72-79 | 10.00 |
| 6 | 212 | 0.40 | 110 | 0.70 | 69-76 | 7.66 |

The polycarbamate products of Examples 3-6 were then combined to yield a total of 1758 g of combined product having a viscosity of 45,374 cP (or 45.4 Pa·sec). The 1758 g of polycarbamate intermediate were diluted with 750 g of THF for viscosity reduction in the subsequent thiolation reactions.

Examples 7-12

Polythiol Composition Produced from a Polycarbamate and $H_2S$

Examples 7-12 were conducted in a manner similar to that of Example 2, but using the 5-L UV autoclave reactor. The combined polycarbamate intermediate of Examples 3-6, diluted with THF, was used as the starting material. Table III summarizes certain process conditions for Examples 7-12. Four different $H_2S$ to olefin double bond ratios were tested, ranging from 30:1 to 100:1. As with Example 2, TEP and Irgacure® 500 photoinitiator were utilized in the UV-initiated reactions of Examples 7-12. The reaction was monitored by Raman spectroscopy for olefin group disappearance at 1646 $cm^{-1}$. The crude reactor samples were stripped on a rotary evaporator to remove the THF solvent and passed through the wiped-film evaporator to remove the phosphorus compounds.

Since Examples 7 and 11-12 were conducted at the same (30:1) $H_2S$/olefin ratio, these three polythiol compositions were blended together before product analysis. The weight percent of thiol product and mono-sulfide dimer was calculated from the titrated mercaptan sulfur and total sulfur values. The average molecular weight, functionality, and viscosity also were determined for the polythiol compositions. Analytical results for the polythiol compositions of Examples 2 and 7-12 are summarized in Table IV.

Unexpectedly, the polythiol compositions of Examples 8-12 were fairly consistent, even with the different $H_2S$/olefin ratios. The polythiol composition of Example 2 resulted in higher sulfide dimer content and molecular weight, which may be attributable to less solvent dilution, use of acetone instead of THF, a higher level of TEP, and/or a lower level of Irgacure® 500. Generally, and without being limited to theory, it was expected that an increase in the ratio of $H_2S$ to carbon-carbon double bonds can be used to increase the average thiol sulfur to sulfide sulfur molar ratio and/or the average thiol sulfur content of the sulfur-containing compounds in the polythiol compositions disclosed herein. However, and unexpectedly, lower ratios of $H_2S$ to carbon-carbon double bonds (e.g., 30:1-50:1 as compared to 70:1-100:1) generally resulted in compositions with higher average thiol sulfur to sulfide sulfur molar ratios, higher average thiol sulfur content, as well as lower mercaptan equivalent weight, lower functionality, and lower average sulfide sulfur content of the sulfur-containing compounds in the polythiol compositions.

TABLE III

Reaction conditions for Examples 7-12

| Example Number | 7 | 8 | 9 | 10 | 11 | 12 |
|---|---|---|---|---|---|---|
| Solution of carbamate + THF (g) | 570 | 370 | 270 | 190 | 543 | 520 |
| $H_2S$ (kg) | 2.6 | 2.8 | 2.9 | 3.1 | 2.6 | 2.6 |
| Ratio of $H_2S$/olefin | 30 | 50 | 70 | 100 | 31 | 33 |
| TEP (g) | 2.0 | 1.3 | 1.0 | 0.7 | 2.0 | 2.0 |
| Wt. % TEP | 0.55 | 0.55 | 0.55 | 0.55 | 0.55 | 0.55 |
| Irgacure 500 (g) | 2.0 | 1.3 | 1.0 | 0.7 | 2.0 | 2.0 |
| Wt. % Irgacure | 0.55 | 0.55 | 0.55 | 0.55 | 0.55 | 0.55 |
| Reaction Time (min) | 15 | 11 | 9 | 9 | 13 | 13 |
| % Conversion (Raman) | 100 | 100 | 100 | 100 | 100 | 100 |

TABLE IV

Polythiol Compositions of Examples 2 and 7-12

| Example Number | 2 | 8 | 9 | 10 | 7 + 11 + 12 |
|---|---|---|---|---|---|
| $H_2S$/olefin equiv ratio | 50 | 50 | 70 | 100 | 30 |
| Viscosity, cP | — | 108,600 | 133,200 | 105,900 | 172,000 |
| Analytical Results | | | | | |
| Total % SH | 14.30% | 14.75% | 14.77% | 14.55% | 14.46% |
| % Total Sulfur | 15.56% | 15.28% | 15.66% | 15.39% | 14.74% |
| monomer wt. % | 40.60% | 73.61% | 57.51% | 59.13% | 85.36% |
| dimer wt. % | 59.40% | 26.39% | 42.49% | 40.87% | 14.64% |
| monomer mol % | 57.2% | 84.5% | 72.6% | 73.9% | 91.9% |
| dimer mol % | 42.8% | 15.5% | 27.4% | 26.1% | 8.1% |
| Avg. Mol. Wt. (g/mol) | 1109 | 904 | 994 | 984 | 848 |
| Avg. Functionality | 4.86 | 4.31 | 4.55 | 4.52 | 4.16 |
| Thiol eq wt. | 228 | 210 | 218 | 218 | 204 |
| Thiol Number, mKOH/g | 246 | 268 | 257 | 258 | 275 |

The invention is described herein with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1

A polythiol composition comprising sulfur-containing compounds having formula (I):

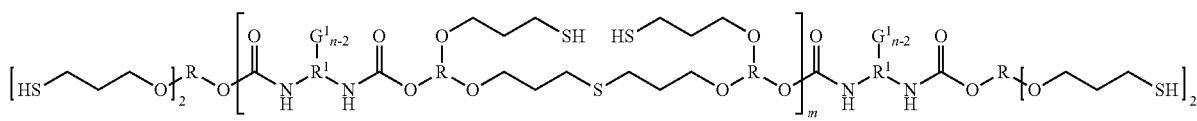

-continued wherein: $G^1$ is 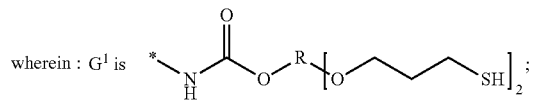  (II)

each R independently is a $C_3$ to $C_{15}$ hydrocarbon group;
each $R^1$ independently is a $C_1$ to $C_{30}$ hydrocarbon group;
n is an integer greater than or equal to 2; and
m is an integer from 0 to 6, wherein an average value of m in the composition is from greater than 0 to 3.

Embodiment 2

A process for producing a polythiol composition, the process comprising:
(1) contacting a compound having the formula

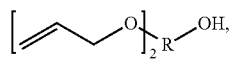  (A)

with a compound having the formula

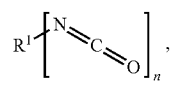  (B)

to form a reaction mixture comprising a polycarbamate; and
(2) contacting the polycarbamate, $H_2S$, and an optional phosphite compound to form the polythiol composition; wherein:
a molar ratio of $H_2S$ to carbon-carbon double bonds of the polycarbamate is in a range from 2:1 to 500:1; and
the polythiol composition comprises sulfur-containing compounds having formula (I):

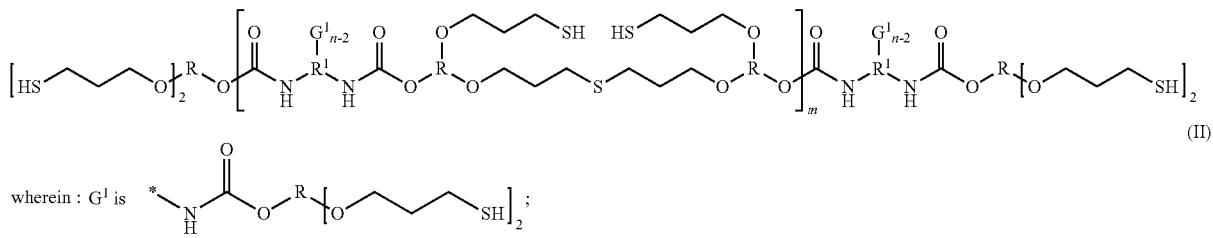

wherein: $G^1$ is 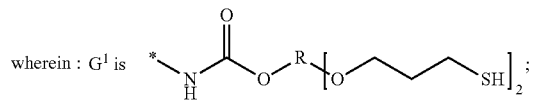  (II)

each R independently is a $C_3$ to $C_{15}$ hydrocarbon group;
each $R^1$ independently is a $C_1$ to $C_{30}$ hydrocarbon group;
n is an integer greater than or equal to 2; and
m is an integer from 0 to 6, wherein an average value of m in the composition is from greater than 0 to 3.

Embodiment 3

The composition or process defined in embodiment 1 or 2, wherein the sulfur-containing compounds of the polythiol composition have an average thiol sulfur (—SH) to sulfide sulfur (—S—) molar ratio in any range of average thiol sulfur to sulfide sulfur molar ratios disclosed herein, e.g., from 2:1 to 500:1, from 3:1 to 100:1, from 5:1 to 75:1, etc.

Embodiment 4

The composition or process defined in any one of the preceding embodiments, wherein the sulfur-containing compounds of the polythiol composition have an average weight percentage of sulfide sulfur (—S—) in any range of average weight percentages of sulfide sulfur disclosed herein, e.g., from 0.05 to 10 wt. %, from 0.1 to 5 wt. %, from 0.1 to 2 wt. %, etc.

Embodiment 5

The composition or process defined in any one of the preceding embodiments, wherein the sulfur-containing compounds of the polythiol composition have an average weight percentage of thiol sulfur (—SH) in any range of average weight percentages of thiol sulfur disclosed herein, e.g., from 12.5 to 16.2 wt. %, from 13 to 16 wt. %, from 14 to 15 wt. %, etc.

Embodiment 6

The composition or process defined in any one of the preceding embodiments, wherein the sulfur-containing compounds of the polythiol composition have a weight percentage of intermolecular sulfide compounds (having a —S— group) in any range disclosed herein, e.g., from 2 wt. % to 90 wt. %, from 5 wt. % to 70 wt. %, from 10 wt. % to 60 wt. %, etc.

Embodiment 7

The composition or process defined in any one of the preceding embodiments, wherein the sulfur-containing compounds of the polythiol composition have a weight percentage of compounds with a thiol sulfur group (—SH), but no sulfide sulfur groups (—S—), in any range disclosed herein, e.g., from 30 wt. % to 95 wt. %, from 40 wt. % to 90 wt. %, from 35 wt. % to 85 wt. %, etc.

Embodiment 8

The composition or process defined in any one of the preceding embodiments, wherein the sulfur-containing compounds of the polythiol composition have a thiol equivalent weight (SHEW) in any range of SHEW's disclosed herein, e.g., from 198 to 300 g/eq, from 200 to 275 g/eq, from 200 to 250 g/eq, etc.

Embodiment 9

The composition or process defined in any one of the preceding embodiments, wherein the sulfur-containing compounds of the polythiol composition have an average thiol functionality in any range of thiol functionalities disclosed herein, e.g., from 4.05 to 6, from 4.05 to 5, from 4.1 to 4.9, etc.

Embodiment 10

The composition or process defined in any one of the preceding embodiments, wherein each R independently is any $C_3$ to $C_{12}$ hydrocarbon group or $C_3$ to $C_{10}$ hydrocarbon group disclosed herein; or alternatively, any $C_3$ to $C_{15}$ alkane group, $C_3$ to $C_{12}$ alkane group, or $C_3$ to $C_{10}$ alkane group disclosed herein.

Embodiment 11

The composition or process defined in any one of the preceding embodiments, wherein each R independently is linear or branched; alternatively, linear; alternatively, branched; alternatively, acyclic or cyclic; alternatively, acyclic; or alternatively, cyclic.

Embodiment 12

The composition or process defined in any one of the preceding embodiments, wherein each R is the same.

Embodiment 13

The composition or process defined in any one of the preceding embodiments, wherein each $R^1$ independently is any $C_1$ to $C_{20}$ hydrocarbon group, $C_1$ to $C_{15}$ hydrocarbon group, or $C_1$ to $C_{10}$ hydrocarbon group disclosed herein; or alternatively, any $C_1$ to $C_{30}$ alkane group, $C_1$ to $C_{20}$ alkane group, $C_1$ to $C_{15}$ alkane group, or $C_1$ to $C_{10}$ alkane group disclosed herein.

Embodiment 14

The composition or process defined in embodiment 13, wherein each $R^1$ independently is linear or branched; alternatively, linear; or alternatively, branched.

Embodiment 15

The composition or process defined in any one of embodiments 1-13, wherein each $R^1$ independently is any aliphatic $C_4$ to $C_{30}$ cyclohydrocarbon group (or cycloalkane group), aliphatic $C_5$ to $C_{20}$ cyclohydrocarbon group (or cycloalkane group), or aliphatic $C_6$ to $C_{12}$ cyclohydrocarbon group (or cycloalkane group) disclosed herein.

Embodiment 16

The composition or process defined in any one of embodiments 1-13, wherein each $R^1$ independently is any $C_6$ to $C_{30}$ aromatic group, $C_6$ to $C_{20}$ aromatic group, or $C_6$ to $C_{12}$ aromatic group disclosed herein.

Embodiment 17

The composition or process defined in any one of the preceding embodiments, wherein each $R^1$ is the same.

Embodiment 18

The composition or process defined in any one of the preceding embodiments, wherein n is any integer disclosed herein, e.g., from 2 to 4, from 2 to 3, equal to 2, equal to 3, etc.

Embodiment 19

The composition or process defined in any one of the preceding embodiments, wherein an average value of n in the composition is in any range disclosed herein, e.g. from 2 to 4, from 2 to 3, etc.

Embodiment 20

The composition or process defined in any one of the preceding embodiments, wherein m is any integer disclosed herein, e.g., from 0 to 4, from 0 to 3, from 0 to 2, etc.

Embodiment 21

The composition or process defined in any one of the preceding embodiments, wherein an average value of m in the compositions is in any range disclosed herein, e.g. from greater than 0 to less than 3, from greater than 0 to 2, from greater than 0 to 1.

Embodiment 22

The composition or process defined in any one of the preceding embodiments, wherein the polythiol composition comprises sulfur-containing compounds having formula (III):

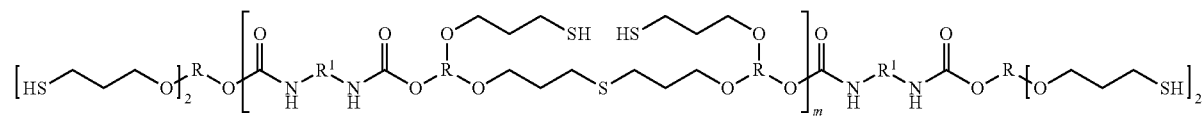

Embodiment 23

The composition or process defined in any one of the preceding embodiments, wherein the sulfur-containing compounds of the polythiol composition comprise:

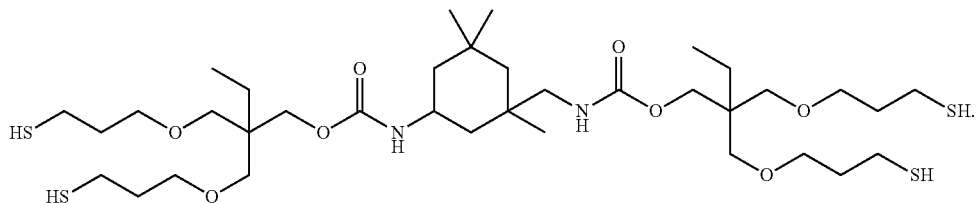 [SMILES: CCC(COCCCS)(COCCCS)COC(=O)NCC1(C)CC(NC(=O)OCC(CC)(COCCCS)COCCCS)CC(C)(C)C1]

Embodiment 24

The composition or process defined in embodiment 23, wherein the sulfur-containing compounds of the polythiol composition further comprise:

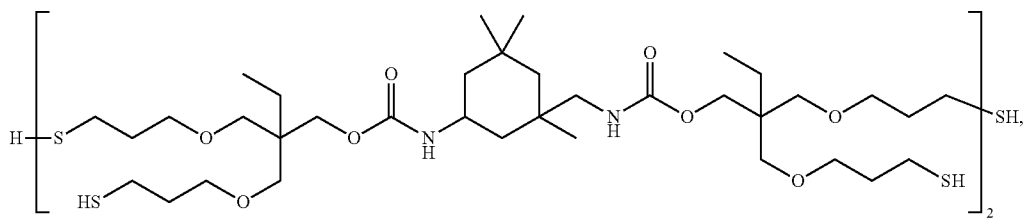

Embodiment 25

The process defined in any one of embodiments 2-24, wherein the process further comprises a step of removing at least a portion of the $H_2S$, of the phosphite compound (if used), of compounds having no sulfur atoms, or combinations thereof, from the polythiol composition.

Embodiment 26

The process defined in embodiment 25, wherein the $H_2S$, the phosphite compound (if used), the compounds having no sulfur atoms, or combinations thereof, are removed by wiped film evaporation, distillation, short path distillation, or a combination thereof.

Embodiment 27

The process defined in any one of embodiments 2-26, wherein the molar ratio of $H_2S$ to carbon-carbon double bonds of the polycarbamate is in any range of molar ratios of $H_2S$ to carbon-carbon double bonds disclosed herein, e.g., from 2:1 to 150:1, from 3:1 to 250:1, from 10:1 to 100:1, etc.

Embodiment 28

The process defined in any one of embodiments 2-27, wherein a molar ratio of the phosphite compound to carbon-carbon double bonds of the polycarbamate is in any range of molar ratios of the phosphite compound to carbon-carbon double bonds disclosed herein, e.g., from 0.0005:1 to 0.10:1, from 0.005:1 to 0.05:1, etc.

Embodiment 29

The process defined in embodiment 28, wherein the phosphite compound comprises a compound having the formula, $P(OR^A)_3$, wherein each $R^A$ is independently any $C_1$-$C_{10}$ hydrocarbyl group disclosed herein.

Embodiment 30

The process defined in embodiment 28, wherein the phosphite compound comprises trimethylphosphite, triethylphosphite, tributylphosphite, or any combination thereof.

Embodiment 31

The process defined in any one of embodiments 2-30, wherein the polythiol composition is formed at a temperature in any range of temperatures disclosed herein, e.g., from −30° C. to 150° C., from −20° C. to 130° C., from −10° C. to 100° C., from −5° C. to 80° C., from 0° C. to 60° C., etc.

Embodiment 32

The process defined in any one of embodiments 2-31, wherein the polythiol composition is formed in the presence of electromagnetic radiation.

Embodiment 33

The process defined in any one of embodiments 2-31, wherein the polythiol composition is formed in the presence of ultraviolet light.

Embodiment 34

The process defined in any one of embodiments 2-31, wherein the polythiol composition is formed in the presence of ultraviolet light and a photoinitiator, and wherein the photoinitiator is present at an amount within any weight percentage range disclosed herein, e.g., less than or equal to 5 wt. %, less than or equal to 3 wt. %, less than or equal to 2 wt. %, less than or equal to 1.5 wt. %, less than or equal to 1.25 wt. %, less than or equal to 1 wt. %, less than or equal to 0.75 wt. %, less than or equal to 0.5 wt. %, etc., based on the weight of the polycarbamate.

Embodiment 35

The process defined in any one of embodiments 2-31, wherein the polythiol composition is formed in the presence of a free radical initiator, and wherein the free radical initiator is present at an amount within any weight percentage range disclosed herein, e.g., from 0.1 to 9 wt. %, from 0.1 to 2 wt. %, etc., based on the weight of the polycarbamate.

Embodiment 36

The process defined in embodiment 35, wherein the polythiol composition is formed at conditions suitable for a thermal decomposition of the free radical initiator.

Embodiment 37

The process defined in any one of embodiments 2-36, wherein the polythiol composition is formed in the presence of any solvent disclosed herein, e.g., a hydrocarbon solvent, an aromatic hydrocarbon solvent, a ketone solvent, an ether solvent, or any combination thereof.

Embodiment 38

The process defined in any one of embodiments 2-37, wherein at least 90%, at least 95%, at least 98%, etc., of the carbon-carbon double bonds of the polycarbamate are converted to a sulfur-containing group.

Embodiment 39

The process defined in any one of embodiments 2-38, wherein the polycarbamate comprises compounds having formula (C):

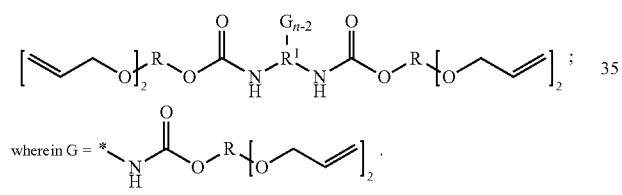

Embodiment 40

The process defined in any one of embodiments 2-39, wherein the polycarbamate comprises compounds having formula (D):

Embodiment 41

The process defined in any one of embodiments 2-40, wherein the compound having formula (A) comprises bis (allyl ether) of trimethylolpropane, bis(allyl ether) of glycerol, bis(allyl ether) of trimethylolethane, bis(allyl ether) of trimethylolmethane, etc., as well as combinations thereof.

Embodiment 42

The process defined in any one of embodiments 2-41, wherein the compound having formula (A) comprises:

Embodiment 43

The process defined in any one of embodiments 2-42, wherein the compound having formula (B) comprises any aliphatic isocyanate (e.g., any cycloaliphatic isocyanate) disclosed herein.

Embodiment 44

The process defined in any one of embodiments 2-43, wherein the compound having formula (B) comprises:

Embodiment 45

The process defined in any one of embodiments 2-44, wherein the polycarbamate comprises:

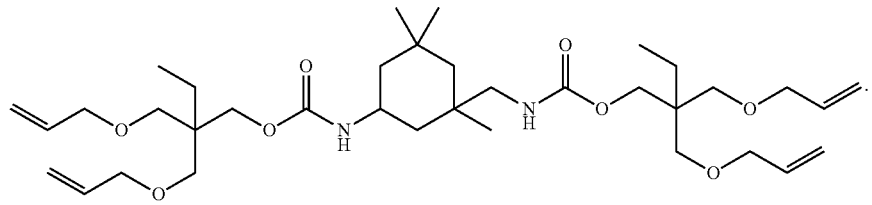 [SMILES: C=CCOCC(CC)(COCC=C)COC(=O)NCC1(C)CC(NC(=O)OCC(CC)(COCC=C)COCC=C)CC(C)(C)C1]

Embodiment 46

The process defined in any one of embodiments 2-45, wherein the equivalent ratio of the compound having formula (A) to the compound having formula (B) is in any range of equivalent ratios of the compound having formula (A) to the compound having formula (B) disclosed herein, e.g., from 0.9:1 to 1.5:1, from 0.95:1 to 1.25:1, from 0.97:1 to 1.15:1, etc.

Embodiment 47

The process defined in any one of embodiments 2-46, wherein the polythiol composition defined in any one of embodiments 1-24 is produced.

Embodiment 48

The composition defined in any one of embodiments 1-24 produced by the process defined in any one of embodiments 2-46.

Embodiment 49

An article of manufacture comprising the composition defined in any one of embodiments 1-24 and 48.

Embodiment 50

An article of manufacture comprising the composition defined in any one of embodiments 1-24 and 48, wherein the article is a coating, a paint, or an adhesive.

We claim:

1. A polythiol composition comprising sulfur-containing compounds having formula (I):

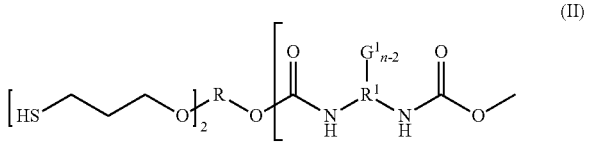

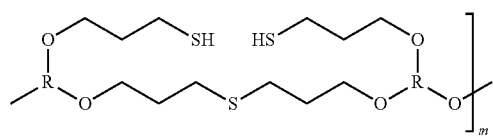

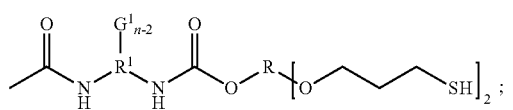

each R independently is a $C_3$ to $C_{15}$ hydrocarbon group;
each $R^1$ independently is a $C_1$ to $C_{30}$ hydrocarbon group;
n is an integer greater than or equal to 2; and
m is an integer from 0 to 6, wherein an average value of m in the composition is from greater than 0 to 3.

2. The composition of claim 1, wherein:
each R independently is a $C_3$ to $C_{15}$ alkane group;
each $R^1$ independently is a substituted or unsubstituted $C_5$ to $C_{20}$ cycloalkane group;
n is an integer from 2 to 4; and
m is an integer from 0 to 4, wherein an average value of m in the composition is from greater than 0 to 2.

3. The composition of claim 1, wherein:
each R is the same and is a $C_3$ to $C_{12}$ alkane group;
each $R^1$ is the same and is a substituted or unsubstituted $C_6$ to $C_{12}$ cycloalkane group;
n is an integer from 2 to 4; and
m is an integer from 0 to 3, wherein an average value of m in the composition is from greater than 0 to 1.

4. The composition of claim 3, wherein n is equal to 2.

5. The composition of claim 1, wherein the sulfur-containing compounds are characterized by:
an average thiol sulfur to sulfide sulfur molar ratio in a range from 2:1 to 500:1;
an average of from 0.05 wt. % to 10 wt. % sulfide sulfur;
an average of from 12.5 wt. % to 16.2 wt. % thiol sulfur;
a thiol equivalent weight in a range from 198 to 300 g/eq; and
an average thiol functionality in a range from 4.05 to 6.

6. The composition of claim 1, wherein the sulfur-containing compounds are characterized by:
an average thiol sulfur to sulfide sulfur molar ratio in a range from 3:1 to 100:1;
an average of from 0.1 wt. % to 5 wt. % sulfide sulfur;
an average of from 13 wt. % to 16 wt. % thiol sulfur;
a thiol equivalent weight in a range from 200 to 250 g/eq; and
an average thiol functionality in a range from 4.05 to 5.

7. The composition of claim 6, wherein n is equal to 2.

8. The composition of claim 1, wherein the sulfur-containing compounds contain from 5 wt. % to 70 wt. % compounds having a sulfide sulfur group.

9. The composition of claim 1, wherein the sulfur-containing compounds contain from 30 wt. % to 95 wt. % compounds having a thiol sulfur group and no sulfide sulfur group.

10. An article of manufacture comprising the polythiol composition of claim 1.

11. The article of claim 10, wherein the article is a coating, a paint, or an adhesive.

12. The composition of claim 1, wherein the sulfur-containing compounds of the polythiol composition comprise:

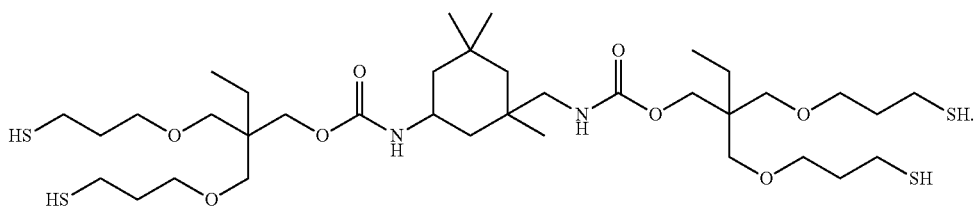 [SMILES: CCC(COCCCS)(COCCCS)COC(=O)NCC1(C)CC(NC(=O)OCC(CC)(COCCCS)COCCCS)CC(C)(C)C1]

13. The composition of claim 12, further comprising a sulfur-containing compound having the structure

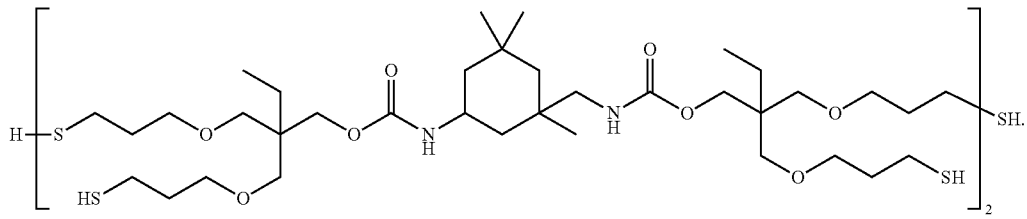

14. An article of manufacture comprising the polythiol composition of claim 13.

15. A process for producing a polythiol composition, the process comprising:

(1) contacting a compound having the formula

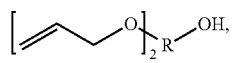 (A)

with a compound having the formula

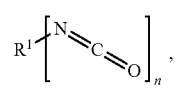 (B)

to form a reaction mixture comprising a polycarbamate; and (2) contacting the polycarbamate, $H_2S$, and an optional phosphite compound to form the polythiol composition; wherein:

a molar ratio of $H_2S$ to carbon-carbon double bonds of the polycarbamate is in a range from 2:1 to 500:1; and the polythiol composition comprises sulfur-containing compounds having formula (I):

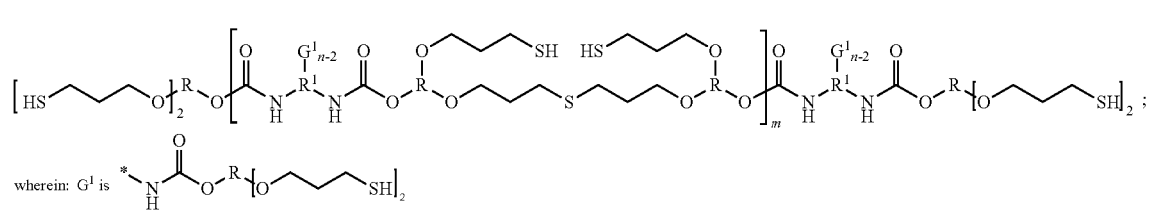 (II)

each R independently is a $C_3$ to $C_{15}$ hydrocarbon group;
each $R^1$ independently is a $C_1$ to $C_{30}$ hydrocarbon group;
n is an integer greater than or equal to 2; and
m is an integer from 0 to 6, wherein an average value of m in the composition is from greater than 0 to 3.

16. The process of claim 15, wherein:
the molar ratio of $H_2S$ to carbon-carbon double bonds of the polycarbamate is in a range from 10:1 to 150:1; and
the polythiol composition is formed in the presence of ultraviolet light.

17. The process of claim 15, wherein the polycarbamate comprises a compound having formula (D):

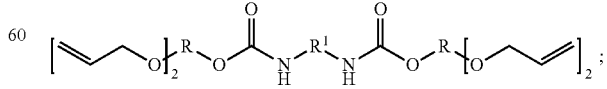

wherein:
each R independently is a $C_3$ to $C_{15}$ hydrocarbon group; and
$R^1$ is $C_1$ to $C_{30}$ hydrocarbon group.

18. The process of claim 15, wherein the polycarbamate comprises:

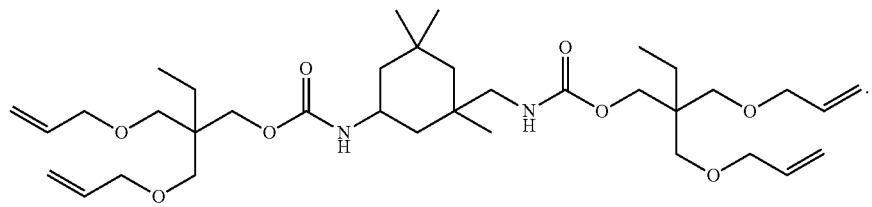 [SMILES: C=CCOCC(CC)(COCC=C)COC(=O)NCC1(C)CC(NC(=O)OCC(CC)(COCC=C)COCC=C)CC(C)(C)C1]

19. The process of claim 15, wherein:

the compound having formula (A) comprises:

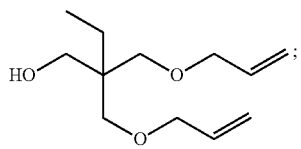

and the compound having formula (B) comprises:

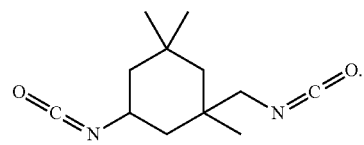 [SMILES: CC1(C)CC(N=C=O)CC(C)(CN=C=O)C1]

20. The process of claim 15, wherein the process further comprises a step of removing at least a portion of the $H_2S$, of the optional phosphite compound, of compounds having no sulfur atoms, or combinations thereof, from the polythiol composition.

* * * * *